United States Patent
Ma et al.

(10) Patent No.: US 11,623,907 B2
(45) Date of Patent: Apr. 11, 2023

(54) METHOD FOR DIRECTLY CONSTRUCTING HIGHLY OPTICALLY ACTIVE TETRASUBSTITUTED ALLENIC ACID COMPOUNDS

(71) Applicant: FUDAN UNIVERSITY, Shanghai (CN)

(72) Inventors: Shengming Ma, Shanghai (CN); Weifeng Zheng, Shanghai (CN); Hui Qian, Shanghai (CN)

(73) Assignee: FUDAN UNIVERISTY, Shanghai (CN)

( * ) Notice: Subject to any disclaimer, the term of this patent is extended or adjusted under 35 U.S.C. 154(b) by 0 days.

(21) Appl. No.: 17/299,082

(22) PCT Filed: Dec. 4, 2019

(86) PCT No.: PCT/CN2019/123005
§ 371 (c)(1),
(2) Date: Jun. 2, 2021

(87) PCT Pub. No.: WO2020/119549
PCT Pub. Date: Jun. 18, 2020

(65) Prior Publication Data
US 2022/0064096 A1    Mar. 3, 2022

(30) Foreign Application Priority Data
Dec. 12, 2018    (CN) .......................... 201811517414.6

(51) Int. Cl.
*C07C 51/12* (2006.01)
*C07B 53/00* (2006.01)
*C07C 51/14* (2006.01)

(52) U.S. Cl.
CPC .............. *C07C 51/12* (2013.01); *C07B 53/00* (2013.01); *C07C 51/14* (2013.01); *C07B 2200/07* (2013.01)

(58) Field of Classification Search
CPC ... C07B 2200/07; C07B 53/00; C07D 307/58; C07D 333/24; G06F 3/0604; G06F 3/0619; G06F 3/064; G06F 3/0658; G06F 3/0659; G06F 3/0679; G11C 11/5642; G11C 11/5671; G11C 16/0483; G11C 16/10; G11C 16/14; G11C 16/24; G11C 16/26; G11C 16/30; G11C 2211/563; G11C 16/08; H01L 27/11556; H01L 27/11582; C07C 253/30; C07C 255/36; C07C 255/41; C07C 51/12; C07C 51/14; C07C 57/42; C07C 57/60; C07C 2602/10
See application file for complete search history.

(56) References Cited

PUBLICATIONS

Tap et al. (Chiral Allenes via Alkynylogous Mukaiyama Aldol Reaction (Organocatalysis, Angewandte, 128, pp. 1-5, Published 2016 (Year: 2016).*
Zheng et al. (Tetrasubstituted allenes via the palladium-catalysed kinetic resolution of propargylic alcohols using a supporting ligand, Nature Catalysis, vol. 2, pp. 997-1005, Published Nov. 2019) (Year: 2019).*
Zheng et al. (2,3-Allenoic acids via palladium-catalyzed carboxylation of propargylic alcohols), Organic Chemistry Frontiers, pp. 1-6 pages, Published Apr. 2018) (Year: 2018).*
Schlenk Tumblr one page, Published 2017 (Year: 2017).*
Tumblr one page Published 2013 (Year: 2013).*
Hawach, seven pages, Published 2019 (Year: 2019).*
Hashimoto et al., "Phase-transfer-catalysed asymmetric synthesis of tetrasubstituted allenes," Nature Chemistry, 2013, pp. 1-5, 5 pages total.
Tap et al., "Chiral Allenes via Alkynylogous Mukaiyama Aldol Reaction," Angewandte Chemie, vol. 128, 2016, pp. 1-5, 5 pages total.
Zheng et al., "2,3-Allenoic acids via palladium-catalyzed carboxylation of propargylic alcohols," Organic Chemistry Frontiers, 2018, pp. 1-5, 6 pages total.

* cited by examiner

*Primary Examiner* — Yevgeny Valenrod
*Assistant Examiner* — Blaine G Doletski
(74) *Attorney, Agent, or Firm* — Birch, Stewart, Kolasch & Birch, LLP

(57) ABSTRACT

The present invention discloses a method for directly constructing highly optically active tetrasubstituted allenic acid compounds, i.e., a one-step process for directly constructing highly optically active axially chiral tetrasubstituted allenic acid compounds by using tertiary propargyl alcohol, carbon monoxide and water as reactants in an organic solvent in the presence of palladium catalyst, chiral diphosphine ligand, monophosphine ligand and organic phosphoric acid. The method of the present invention has the following advantages: operations are simple, raw materials and reagents are readily available, the reaction conditions are mild, the substrate has high universality, the functional group has good compatibility, and the reaction has high enantioselectivity (90%~>99% ee). The highly optically active allenic acid compounds obtained by the present invention can be used as an important intermediate to construct γ-butyrolactone compounds containing tetrasubstituted chiral quaternary carbon centers, tetrasubstituted allenic alcohol and other compounds.

17 Claims, No Drawings

METHOD FOR DIRECTLY CONSTRUCTING HIGHLY OPTICALLY ACTIVE TETRASUBSTITUTED ALLENIC ACID COMPOUNDS

TECHNICAL FIELD

The present invention belongs to the technical field of chemical synthesis, particularly to a method for directly constructing highly optically active tetrasubstituted allenic acid compounds.

BACKGROUND OF THE INVENTION

Axially chiral allene compounds are widely consisted in natural products and drug molecules. They are a very important class of compounds (Ref: (a) Hoffmann-Roder, A.; Krause, N. Angew. Chem., Int. Ed. 2004, 43, 1196. (b) Rivera-Fuentes, P.; Diederich, F. Angew. Chem., Int. Ed. 2012, 51, 2818). How to construct tetra-substituted chiral quaternary carbon centers has been widely researched in the past ten years and achieved fruitful results. However, compared with the construction of compounds containing tetra-substituted chiral quaternary carbon centers, the synthesis of tetrasubstituted axial chiral allene compounds is still a big challenge, and the reported methods are still very limited, mainly because the allene molecule contains a cumulative carbon-carbon double bond that is perpendicular to each other in space. The substituents at the 1,3-position of the allenyl group are located in relatively distant space and perpendicular to each other, compared with the formation of central chirality, it needs a larger chiral shielding environment to induce the formation of axial chirality (Ref: (a) Hayashi, T.; Tokunaga, N.; Inoue, K. Org. Lett. 2004, 6, 305. (b) Qian, D.; Wu, L.; Lin, Z.; Sun, J. Nat. Commun. 2017, 8, 567. (c) Hashimoto, T.; Sakata, K.; Tamakuni, F.; Dutton, M. J.; Maruoka, K. Nat. Chem. 2013, 5, 240. (d) Mbofana, C. T.; Miller, S. J. J. Am. Chem. Soc. 2014, 136, 3285. (e) Wang, G.; Liu, X.; Chen, Y.; Yang, J.; Li, J.; Lin, L.; Feng, X. ACS Catal. 2016, 6, 2482. (f) Tang, Y.; Xu, J.; Yang, J.; Lin, L.; Feng, X.; Liu, X. Chem. 2018, 4, 1658. (g) Tap, A.; Blond, A.; Wakchaure, V. N.; List, B. Angew. Chem., Int. Ed. 2016, 55, 8962).

Chiral allenic acid compounds are mainly prepared by the splitting method of racemic allenic acid compounds or allenic nitrile compounds (Ref: (a) Ma, S.; Wu, S. Chem. Commun. 2001, 0, 441. (b) Ao, Y.-F.; Wang, D.-X.; Zhao, L.; Wang, M.-X. J. Org. Chem. 2014, 79, 3103.) and the hydrolysis method of chiral allenic acid ester (Ref: (a) Marshall, J. A.; Bartley, G. S.; Wallace, E. M. J. Org. Chem. 1996, 61, 5729. (b) Yu, J.; Chen, W.-J.; Gong, L.-Z. Org. Lett. 2010, 12, 4050), and the methods above are very limited for the preparation of tetrasubstituted allenic acid compounds. Generally, these methods have some limitations, such as low reaction yield, narrow range of substrates, poor tolerance of functional groups, poor atomic economics and so on. Therefore, the development of a method for synthesizing tetrasubstituted axially chiral allenic acid compounds with high efficiency and high enantioselectivity starting from simple and easily available raw materials will be an important breakthrough to the existing synthetic methods.

SUMMARY OF THE INVENTION

The object of the present invention is to provide a method for directly constructing highly optically active axially chiral tetrasubstituted allenic acid compounds, i.e., a one-step process for directly constructing high optically active axially chiral tetrasubstituted allenic acid compounds by using tertiary propargyl alcohol, carbon monoxide and water as reactants in an organic solvent in the presence of palladium catalyst, chiral diphosphine ligand, monophosphine ligand and organic phosphoric acid.

The object of the present invention is achieved by using the following solution:

The present invention provides a method for directly constructing highly optically active axially chiral tetrasubstituted allenic acid compounds includes: in the presence of palladium catalyst, chiral diphosphine ligand, monophosphine ligand and organic phosphoric acid, the tertiary propargyl alcohol with different substituents, carbon monoxide and water undergo asymmetric allylation reaction in organic solvent through transition metal catalysis, constructing highly optically active axially chiral tetrasubstituted allenic acid compounds in one-step synthesis. The reaction has the following reaction equation (I):

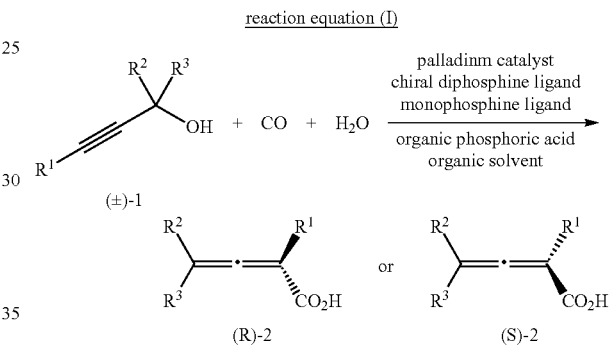

reaction equation (I)

Wherein, $R^1$ is an alkyl, an alkyl with functional group, phenyl, aryl or heterocyclic group; $R^2$ is an alkyl, an alkyl with functional group, phenyl, aryl or heterocyclic group; $R^3$ is an alkyl, an alkyl with functional group, phenyl, aryl or heterocyclic group; the said aryl is a phenyl with electron-donating or electron-withdrawing substituents at the ortho meta and para positions; the said heterocyclic group is thienyl, furyl, naphthyl or pyridyl, or thiophene, furan, naphthalene or pyridine with electron-donating or electron-withdrawing substituents.

Preferably, in the reaction equation (I), $R^1$ is a C1-C20 alkyl, a C1-C20 alkyl with functional group at the end, phenyl, aryl or heterocyclic group; $R^2$ is a C1-C10 alkyl, a C1-C10 alkyl with functional group at the end, phenyl, aryl or heterocyclic group; $R^3$ is a C1-C10 alkyl, a C1-C10 alkyl with functional group at the end, phenyl, aryl or heterocyclic group; wherein, the functional group of the C1-C20 alkyl or C1-C10 alkyl with functional group at the end, is selected from carbon-carbon double bond, carbon-carbon triple bond, ester group, hydroxyl group, acyl group, acyloxy group, amide group, halogen, carboxyl group, cyano group; the said aryl is a phenyl with electron-withdrawing or electron-donating substituents at the ortho, meta, and para positions; the said heterocyclic group is thienyl, furyl, naphthyl or pyridyl, or thiophene, furan, naphthalene or pyridine with electron-withdrawing or electron-donating substituents; the said electron-withdrawing substituent includes halogen, nitro group, ester group, carboxyl group, acyl group, amide group, cyano group; the said electron-donating substituent includes alkyl, alkenyl, phenyl, alkoxy group, hydroxyl, amino group.

More preferably, in the reaction equation (I), $R^1$ is a C1-C10 alkyl, a C1-C10 alkyl with functional group at the end, phenyl, aryl or heterocyclic group; $R^2$ is a C1-C10 alkyl, a C1-C10 alkyl with functional group at the end, phenyl, aryl or heterocyclic group; $R^3$ is a C1-C5 alkyl, a C1-C5 alkyl with functional group at the end, phenyl, aryl or heterocyclic group; wherein, the said alkyl groups of C1-C10 are alkyl, alkenyl, phenyl, aryl or heterocyclic group; the said alkyl groups of C1-C5 are methyl, ethyl, n-propyl (and its isomers), n-butyl (and its isomers) and n-pentyl (and its isomers); the functional group of the C1-C10 alkyl groups or C1-C5 alkyl groups with functional groups at the end, is selected from carbon-carbon double bond, carbon-carbon triple bond, ester group, hydroxyl group, acyl group, acyloxy group, amide group, halogen, carboxyl group, cyano group; said aryl is a phenyl with electron-withdrawing or electron-donating substituents at the ortho, meta, and para positions; the said heterocyclic group is thienyl, furyl, naphthyl or pyridyl, or thiophene, furan, naphthalene or pyridine with electron-withdrawing or electron-donating substituents; the said electron-withdrawing substituent includes halogen, nitro group, ester group, carboxyl group, acyl group, amide group, cyano group; the said electron-donating substituent includes alkyl, alkenyl, phenyl, alkoxy group, hydroxyl, amino group.

More preferably, in the reaction equation (I), $R^1$ is selected from a C1-C10 linear alkyl, a C1-C10 cycloalkyl, a C1-C10 alkyl with functional groups at the end, phenyl, aryl or heterocyclic group; $R^2$ is selected from a C1-C10 linear alkyl, a C1-C10 cycloalkyl, a C1-C10 alkyl with functional groups at the end, phenyl, aryl or heterocyclic group; $R^3$ is selected from a C1-C5 linear alkyl, a C1-C5 cycloalkyl, a C1-C5 alkyl with functional groups at the end, phenyl, aryl or heterocyclic group; the functional group of the C1-C10 alkyl groups or C1-C5 alkyl groups with functional groups at the end, is selected from carbon-carbon double bond, carbon-carbon triple bond, ester group, hydroxyl group, acyl group, acyloxy group, amide group, halogen, carboxyl group, cyano group; the said heterocyclic group is thienyl, furyl, naphthyl or pyridyl, or thiophene, furan, naphthalene or pyridine with electron-withdrawing or electron-donating substituents; the said electron-withdrawing substituent includes halogen, nitro group, ester group, carboxyl group, acyl group, amide group, cyano group; the said electron-donating substituent includes alkyl, alkenyl, phenyl, alkoxy group, hydroxyl, amino group.

More preferably, in the reaction equation (I), $R^1$ is selected from methyl, ethyl, n-propyl, isopropyl, n-butyl, n-amyl, n-hexyl, n-heptyl, n-octyl, phenyl ethyl, 4-chlorobutyl, 3-methylbutyl, 3-cyanopropyl, allyl; $R^2$ is selected from n-propyl, tert-butyl, phenyl, o-methylphenyl, m-methylphenyl, p-methylphenyl, m-methoxyphenyl, p-chlorophenyl, p-bromophenyl, p-ester phenyl, 2-naphthyl, 3-thienyl; $R^3$ is selected from methyl, ethyl.

As a further improvement, the present process comprises the following steps:

(1) a palladium catalyst, a chiral diphosphine ligand, a monophosphine ligand and an organic phosphoric acid are added in sequence into a dried reaction tube, plugging the reaction tube with a rubber stopper, connecting the vacuum pump, replacing argon under argon atmosphere, adding a functionalized tertiary propargyl alcohol, water, and a certain volume of organic solvent; freezing the reaction tube in liquid nitrogen bath, inserting carbon monoxide balloon, replacing carbon monoxide into the reaction system under the atmosphere of carbon monoxide; after freezing and pumping, when the reaction system returns to the room temperature and melts, putting the reaction tube in the preset low-temperature bath or oil bath and stirring.

Wherein, the dosage of the organic solvent is 1.0-10.0 mL/mmol; preferably, is 5.0 mL/mmol. The dosage of functionalized tertiary propargyl alcohol (±1) shown in equation (I) is taken as the basis.

(2) after the completion of the reaction in step (1), raising the reaction tube from the low-temperature bath. After returning to the room temperature, a certain volume of ethyl acetate is added into the reaction tube, filtering the mixture with silica gel short column, washing with a certain amount of ethyl acetate, concentrating, and subjecting to the flash column chromatography, so as to obtain the highly optically active axially chiral allenic acid compounds.

Wherein, the certain volume of the ethyl acetate refers to the amount of functionalized tertiary propargyl alcohol (±1) shown in equation (I), the said amount of ethyl acetate is 1.0-100 mL/mmol; preferably, is 5.0 mL/mmol.

As a further improvement, the palladium catalyst used in the present invention is any one or more of dis-(allyl-palladium chloride), tetra-(triphenylphosphine) palladium, tri-(dibenzylidene-acetone) dipalladium, dis-(cinnamyl-palladium chloride), dis-(dibenzylidene-acetone) monopalladium, palladium chloride, palladium acetate, dis-(triphenylphosphine) palladium chloride, bis-(acetonitrile) palladium chloride, and so on; preferably, palladium chloride.

As a further improvement, the chiral diphosphine ligand used in the present invention is selected from one or more of (R)-L1~(R)-L4 and its enantiomers (S)-L1~(S)-L4 in the following structure; preferably, the chiral diphosphine ligand is (R)-L4 and/or its enantiomer (S)-L4.

Wherein, "Ar" is a phenyl, an aryl or heterocyclic group; the said aryl is a phenyl substituted by alkyl or alkoxy group at the ortho, meta, and para positions; wherein the said alkyl includes methyl, ethyl, propyl, isopropyl, butyl, isobutyl, tert-butyl; the said alkoxy group includes ethoxyl, propoxyl, isopropoxyl, butoxyl, isobutyloxyl, tert butoxyl; the said heterocyclic group is thienyl, furyl or pyridyl; preferably, the said "Ar" is phenyl, 3,5-ditert-butyl-4-methoxyphenyl.

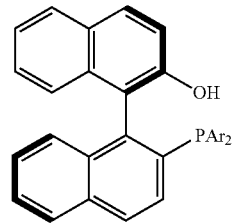

(R)-L1

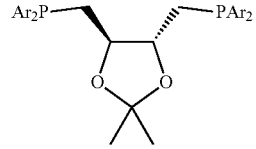

(R)-L2

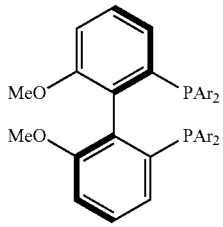

(R)-L3

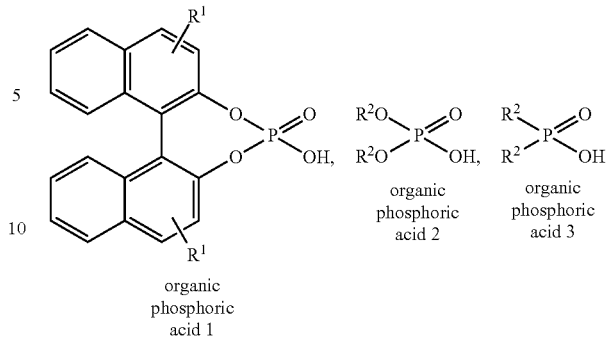

organic phosphoric acid 1, organic phosphoric acid 2, organic phosphoric acid 3

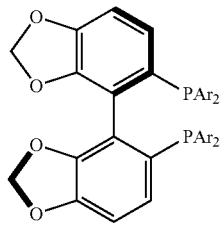

(R)-L4

As a further improvement, the chiral diphosphine ligand used in the present invention is selected from one or more of (R)-L4a, (R)-L4b (R)-L4c and its enantiomer (S)-L4a, (S)-L4b, (S)-L4c; wherein, the structure of the said (R)-L4a, (R)-L4b, (R)-L4c is as follows:

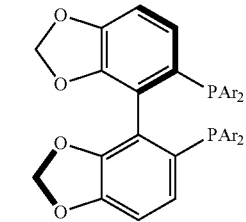

(R)-L4a, Ar = phenyl
(R)-L4b, Ar = 3,5-dimethylphenyl
(R)-L4c, Ar = 3,5-ditert-butyl-4-methoxyphenyl As a further improvement, the monophosphine ligands used in the present invention are selected from tributylphosphine, tricyclohexylphosphine, triphenylphosphine, tris (ortho-methyl-phenyl) phosphine, tris (meta-methyl-phenyl) phosphine, tris (para-methyl-phenyl) phosphine, tris (para-methoxyphenyl) phosphine, tris(3,5-di-tri-fluoromethyl-phenyl) phosphine, trifuryl-phosphine, and so on; preferably, is triphenylphosphine.

As a further improvement, the organic phosphoric acid used in the present invention is selected from any one or more of organic phosphoric acid 1, organic phosphoric acid 2, organic phosphoric acid 3, and so on; wherein, $R^1$ is hydrogen, C1-C6 alkyl, phenyl or aryl; the said aryl is a phenyl substituted by C1-C6 alky at the ortho, meta, and para positions; $R^2$ is C1-C6 alkyl, phenyl or aryl; the said aryl is a phenyl substituted by C1-C6 alky at the ortho, meta, and para positions; preferably, $R^1$ and $R^2$ are phenyl.

As a further improvement, the organic solvent used in the present invention is selected from any one or more of N-methyl pyrrolidone, 1,4-dioxane, tetrahydrofuran, acetonitrile, methyl tert-butyl ether, chlorobenzene, toluene, trifluorotoluene, dichloromethane, 1,1-dichloroethane, 1,2-dichloroethane, chloroform, acetic acid, and so on; preferably, is toluene.

As a further improvement, the said reaction temperature of the present invention is −20~60° C.; preferably, is −20~0° C.; more preferably, is −5~0° C.

As a further improvement, the said reaction time of the present invention is 4-36 hours; preferably, is 18 hours.

As a further improvement, the said molar ratio of tertiary propargyl alcohol (±1) with different substituents, water, palladium catalyst, chiral diphosphine ligand, monophosphine ligand and organic phosphoric acid in equation (I) of the present invention is 1.0: (1.0-30.0): (0.005-0.1): (0.005-0.1): (0.01-0.3): (0.01-0.3); preferably, is 1.0:20.0:0.02: 0.048:0.2:0.2.

The present invention also provides highly optically active axially chiral allenic acid compounds, the structure of which is shown as (R)-2, (S)-2:

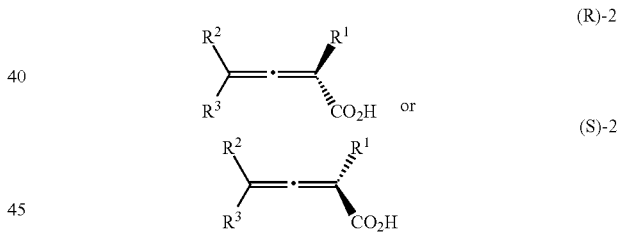

Wherein, $R^1$ is an alkyl, an alkyl with functional group, phenyl, aryl or heterocyclic group; $R^2$ is an alkyl, an alkyl with functional group, phenyl, aryl or heterocyclic group; $R^3$ is an alkyl, an alkyl with functional group, phenyl, aryl or heterocyclic group; the said aryl is a phenyl with electron-donating or electron-withdrawing substituents at the ortho, meta, and para positions; the said heterocyclic group is thienyl, furyl, naphthyl or pyridyl, or thiophene, furan, naphthalene or pyridine with electron-donating or electron-withdrawing substituents.

Preferably, in the reaction equation (I), $R^1$ is a C1-C20 alkyl, a C1-C20 alkyl with functional group at the end, phenyl, aryl or heterocyclic group; $R^2$ is a C1-C10 alkyl, a C1-C10 alkyl with functional group at the end, phenyl, aryl or heterocyclic group; $R^3$ is a C1-C10 alkyl, a C1-C10 alkyl with functional group at the end, phenyl, aryl or heterocyclic group; wherein, the functional group of the C1-C20 alkyl or C1-C10 alkyl with functional group at the end, is selected from carbon-carbon double bond, carbon-carbon triple bond, ester group, hydroxyl group, acyl group, acyloxy group, amide group, halogen, carboxyl group, cyano group;

the said aryl is a phenyl with electron-withdrawing or electron-donating substituents at the ortho, meta, and para positions; the said heterocyclic group is thienyl, furyl, naphthyl or pyridyl, or thiophene, furan, naphthalene or pyridine with electron-withdrawing or electron-donating substituents; the said electron-withdrawing substituent includes halogen, nitro group, ester group, carboxyl group, acyl group, amide group, cyano group; the said electron-donating substituent includes alkyl, alkenyl, phenyl, alkoxy group, hydroxyl, amino group.

More preferably, in the reaction equation (I), $R^1$ is a C1-C10 alkyl, a C1-C10 alkyl with functional group at the end, phenyl, aryl or heterocyclic group; $R^2$ is a C1-C10 alkyl, a C1-C10 alkyl with functional group at the end, phenyl, aryl or heterocyclic group; $R^3$ is a C1-C5 alkyl, a C1-C5 alkyl with functional group at the end, phenyl, aryl or heterocyclic group; wherein, the said alkyl groups of C1-C10 are alkyl, alkenyl, phenyl, aryl or heterocyclic group; the said alkyl groups of C1-C5 are methyl, ethyl, n-propyl (and its isomers), n-butyl (and its isomers) and n-pentyl (and its isomers); the functional group of the C1-C10 alkyl groups or C1-C5 alkyl groups with functional groups at the end, is selected from carbon-carbon double bond, carbon-carbon triple bond, ester group, hydroxyl group, acyl group, acyloxy group, amide group, halogen, carboxyl group, cyano group; the said aryl is a phenyl with electron-withdrawing or electron-donating substituents at the ortho, meta, and para positions; the said heterocyclic group is thienyl, furyl, naphthyl or pyridyl, or thiophene, furan, naphthalene or pyridine with electron-withdrawing or electron-donating substituents; the said electron-withdrawing substituent includes halogen, nitro group, ester group, carboxyl group, acyl group, amide group, cyano group; the said electron-donating substituent includes alkyl, alkenyl, phenyl, alkoxy group, hydroxyl, amino group.

More preferably, in the reaction equation (I), $R^1$ is selected from C1-C10 linear alkyl, C1-C10 cycloalkyl, C1-C10 alkyl with functional groups at the end, phenyl, aryl or heterocyclic group; $R^2$ is selected from C1-C10 linear alkyl, C1-C10 cycloalkyl, C1-C10 alkyl with functional groups at the end, phenyl, aryl or heterocyclic group; $R^3$ is selected from C1-C5 linear alkyl, C1-C5 cycloalkyl, C1-C5 alkyl with functional groups at the end, phenyl, aryl or heterocyclic group; the functional group of the C1-C10 alkyl groups or C1-C5 alkyl groups with functional groups at the end, is selected from carbon-carbon double bond, carbon-carbon triple bond, ester group, hydroxyl group, acyl group, acyloxy group, amide group, halogen, carboxyl group, cyano group; the said heterocyclic group is thienyl, furyl, naphthyl or pyridyl or thiophene, furan, naphthalene or pyridine with electron-withdrawing or electron-donating substituents; the said electron-withdrawing substituent includes halogen, nitro group, ester group, carboxyl group, acyl group, amide group, cyano group; the said electron-donating substituent includes alkyl, alkenyl, phenyl, alkoxy group, hydroxyl, amino group.

More preferably, in the reaction equation (I), $R^1$ is selected from methyl, ethyl, n-propyl, isopropyl, n-butyl, n-amyl, n-hexyl, n-heptyl, n-octyl, phenyl ethyl, 4-chlorobutyl, 3-methylbutyl, 3-cyanopropyl, allyl; $R^2$ is selected from n-propyl, tert-butyl, phenyl, o-methylphenyl, m-methylphenyl, p-methylphenyl, m-methoxyphenyl, p-chlorophenyl, p-bromophenyl, p-ester phenyl, 2-naphthyl, 3-thienyl; $R^3$ is selected from methyl, ethyl.

The present invention also provides the application of the highly optically active axially chiral allenic acid compound shown in formula (R)-2 in the preparation of γ-butyrolactone compounds containing tetrasubstituted chiral quaternary carbon centers, tetrasubstituted allenic alcohol and other compounds.

The present invention proposes the following possible mechanism for the reaction: organic phosphoric acid (HB) activates tertiary propargyl alcohol to form intermediate I, and then palladium species (PDL*) oxidizes it to remove water to form an allenyl palladium intermediate II. Then, the intermediate II reacts with carbon monoxide and water to form intermediate III or intermediate IV, followed by reduction and elimination to obtain optically active tetrasubstituted allenic acid and regenerate palladium species (PDL*). The specific mechanism is shown in the following formula.

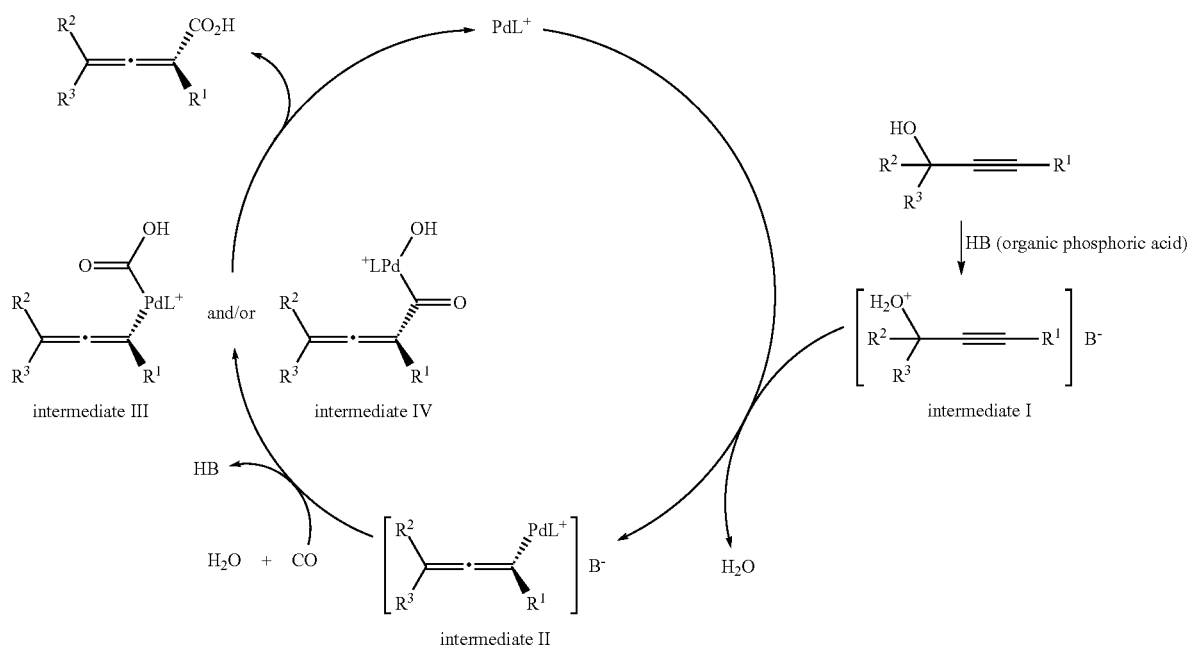

The innovation of the present invention is that the present invention starts from an easily available functionalized tertiary propargyl alcohol as the starting material, a one-step process for directly constructing highly optically active axially chiral tetrasubstituted allenic acid compounds in the presence of palladium catalyst, chiral diphosphine ligand, monophosphine ligand and organic phosphoric acid at the first time. The highly optically active allenic acid compounds obtained by the present invention can be used as an important intermediate to construct γ-butyrolactone compounds containing tetrasubstituted chiral quaternary carbon centers.

The present invention has the following advantages: raw materials and reagents are readily available, preparation is convenient; the reaction conditions are mild, operations are simple; has a broader spectrum of substrates and good compatibility for functional groups; can construct optically pure tetrasubstituted allenic acid compounds containing axial chirality on one step; the product has high enantioselectivity (90% ee~>99% ee); and the product is easy to separate and purify and so on.

PREFERRED EMBODIMENTS OF THE INVENTION

The following examples are given to further illustrating the specific solutions of the present invention. The process, conditions, experimental methods, and so on for implementing the present invention are all general knowledge and common knowledge in the field except for the contents specifically mentioned below, and the present invention has no special limitation. The specific structural formula and the corresponding number of chiral diphosphine ligands involved in all the examples are as follows:

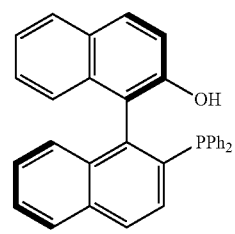

(R)-L1

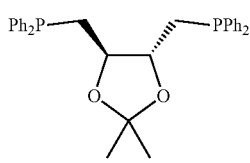

(R)-L2

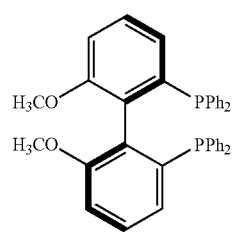

(R)-L3a

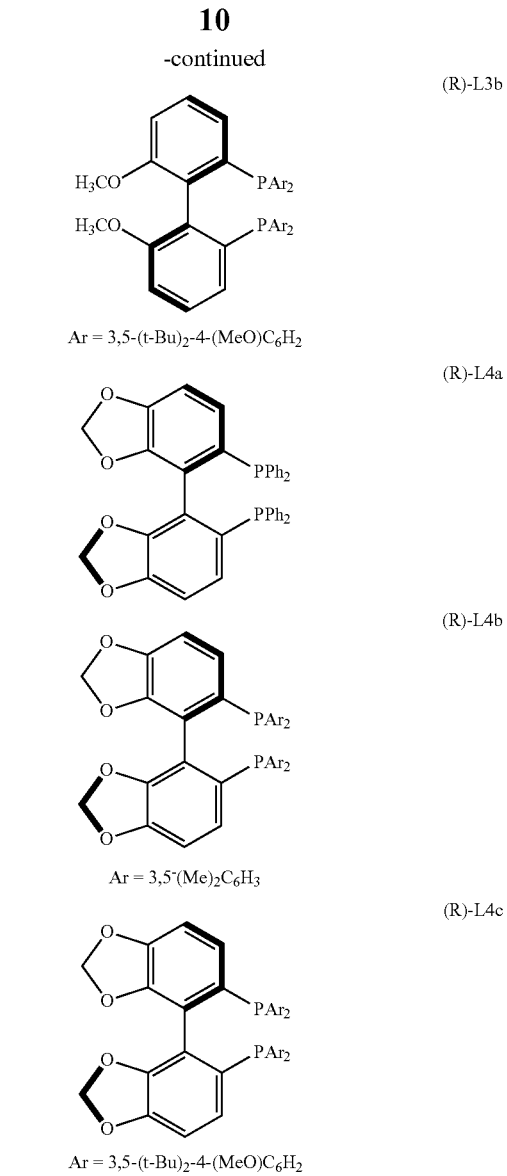

Example 1

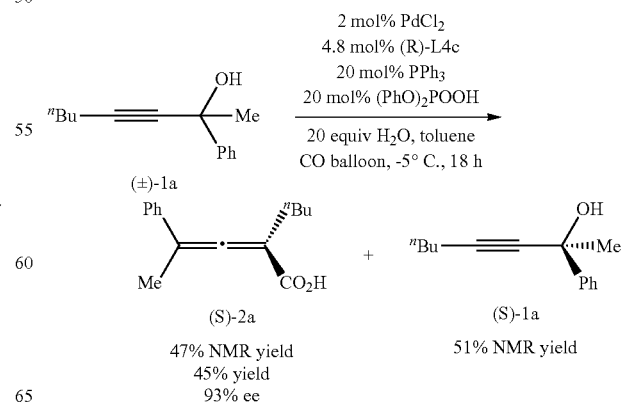

wherein, "mol" refers to mole, "toluene" refers to toluene, "CO balloon" refers to carbon monoxide balloon, "ee" refers to the percentage of enantiomeric excess.

PdCl$_2$ (0.0036 g, 0.02 mmol), chiral diphosphine ligand (R)-L4c (0.057 g, 0.048 mmol), monophosphine ligand PPh$_3$ (0.0527 g, 0.2 mmol), and (PhO)$_2$PO$_2$H (0.0501 g, 0.2 mmol) were added to a dried Schlenk reaction tube. The reaction tube was then plugged with a rubber stopper, and then connected with the vacuum pump, and replaced the argon three times under argon atmosphere. And under the protection of the argon, tertiary propargyl alcohol (±)-1a (0.2016 g, 1 mmol), toluene (3 mL), water (360 μL, d=1.0 g/ml, 0.36 g, 20 mmol) and toluene (2 ml) were added. After closed the argon, freezed the reaction tube in liquid nitrogen bath for 3 minutes, inserted carbon monoxide balloon (about 1 liter), replaced carbon monoxide under the atmosphere of carbon monoxide three times, then removed the liquid nitrogen bath. When the reaction system returned to the room temperature and melted into liquid, putted the reaction tube in the preset −5° C. low temperature bath and stirred for 18 hours. The reaction tube was took out of the low temperature bath, and returned to the room temperature and added H$_2$O$_2$ (40 μL, d=1.13 g/mL, 30 wt. % in H$_2$O, 0.0135 g, 0.4 mmol), stirred at room temperature for 30 minutes. The reaction solution was diluted with ethyl acetate (5 mL), the mixture solution was filtered with silica gel short column (3 cm), and then washed with ethyl acetate (20 mL), concentrated, and subjected to the flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.1033 g, 45%): solid; 93% ee (HPLC conditions: AS-H column, hexane/i-PrOH=98/2, 1.0 mL/min, λ=214 nm, t$_R$ (major)=7.9 min, t$_R$ (minor)=10.0 min); [α]$_D^{26}$=+21.2 (c=1.10, CHCl$_3$). Melting point: 88.4-90.1° C. (measuring directly after solvent evaporates to dryness). $^1$H NMR (400 MHz, d$_6$-DMSO): δ=12.41 (s, 1H, COOH), 7.44-7.32 (m, 4H, Ar—H), 7.32-7.22 (m, 1H, Ar—H), 2.24 (t, J=7.4 Hz, 2H, CH$_2$), 2.12 (s, 3H, CH$_3$), 1.46-1.22 (m, 4H, 2×CH$_2$), 0.84 (t, J=7.0 Hz, 3H, CH$_3$); $^{13}$C NMR (100 MHz, d$_6$-DMSO): δ=210.4, 167.9, 135.2, 128.7, 127.5, 125.8, 103.6, 101.9, 29.9, 28.2, 21.8, 16.3, 13.8; IR (neat): ν=3210-2410 (br), 1935, 1678, 1416, 1279, 1061 cm$^{-1}$; MS (70 eV, EI) m/z (%): 230 (M$^+$, 3.01), 143 (100); Anal. Calcd. for C$_{15}$H$_{18}$O$_2$: C, 78.23, H, 7.88; found: C, 78.03, H, 7.94.

Example 2

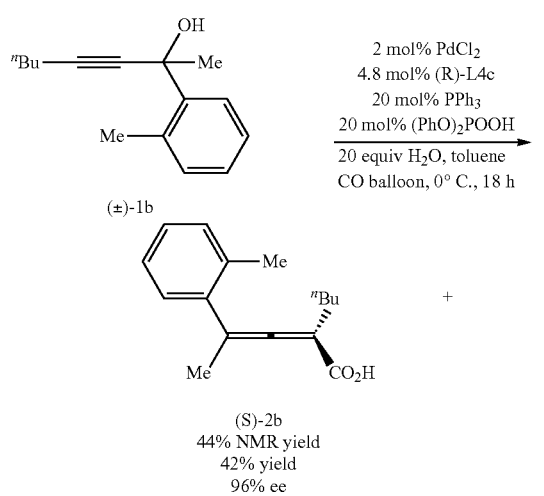

(±)-1b 2 mol% PdCl$_2$
4.8 mol% (R)-L4c
20 mol% PPh$_3$
20 mol% (PhO)$_2$POOH
20 equiv H$_2$O, toluene
CO balloon, 0° C., 18 h (S)-2b
44% NMR yield
42% yield
96% ee -continued

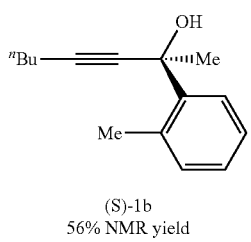

(S)-1b
56% NMR yield

Operations were conducted by referring to Example 1. PdCl$_2$ (0.0036 g, 0.02 mmol), (R)-L4c (0.0564 g, 0.048 mmol), PPh$_3$ (0.0523 g, 0.2 mmol), (PhO)$_2$PO$_2$H (0.05 g, 0.2 mmol), (±)-1b (0.2157 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2b (0.1029 g, 42%): oil substance; 96% ee (HPLC conditions: AS-H column, hexane/i-PrOH=98/2, 1.0 mL/min, λ=214 nm, t$_R$ (major)=6.5 min, t$_R$ (minor)=9.3 min); [α]$_D^{26}$=+106.7 (c=1.50, CHCl$_3$); $^1$H NMR (400 MHz, CDCl$_3$): δ=7.29-7.22 (m, 1H, Ar—H), 7.22-7.12 (m, 3H, Ar—H), 2.40 (s, 3H, CH$_3$), 2.35-2.05 (m, 5H, CH$_2$ and CH$_3$), 1.55-1.40 (m, 2H, CH$_2$), 1.40-1.27 (m, 2H, CH$_2$), 0.90 (t, J=7.2 Hz, 3H, CH$_3$); $^{13}$C NMR (100 MHz, CDCl$_3$): δ=210.2, 173.8, 136.2, 136.0, 130.6, 127.9, 127.6, 125.9, 104.5, 98.9, 30.1, 28.1, 22.2, 20.4, 19.9, 13.8; IR (neat): ν=3200-2410 (br), 1947, 1674, 1415, 1274, 1041 cm$^{-1}$; MS (70 eV, EI) m/z (%): 245 (M$^+$+1, 2.27), 244 (M$^+$, 11.75), 143 (100); HRMS calcd for C$_{16}$H$_{20}$O$_2$ [M$^+$]: 244.1463, found: 244.1467.

Example 3

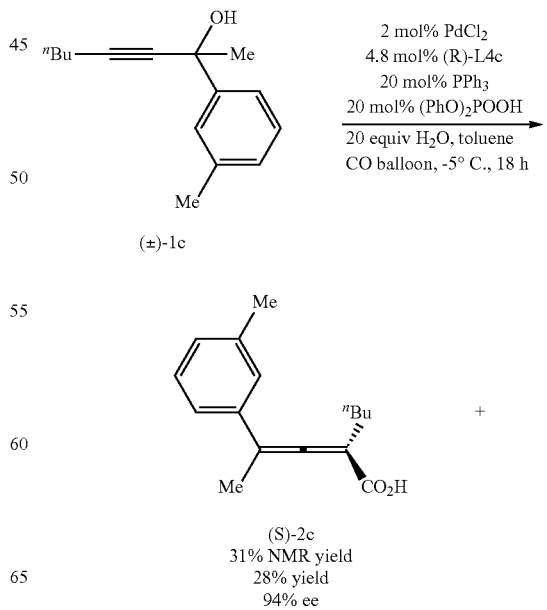

(±)-1c 2 mol% PdCl$_2$
4.8 mol% (R)-L4c
20 mol% PPh$_3$
20 mol% (PhO)$_2$POOH
20 equiv H$_2$O, toluene
CO balloon, -5° C., 18 h (S)-2c
31% NMR yield
28% yield
94% ee

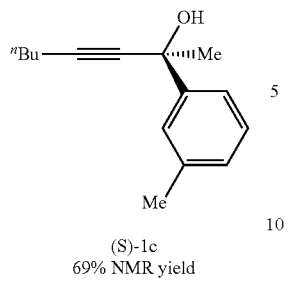

(S)-1c
69% NMR yield

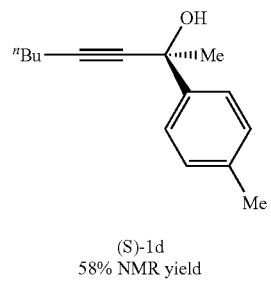

(S)-1d
58% NMR yield

Operations were conducted by referring to Example 1. PdCl$_2$ (0.0036 g, 0.02 mmol), (R)-L4c (0.0571 g, 0.048 mmol), PPh$_3$ (0.0526 g, 0.2 mmol), (PhO)$_2$PO$_2$H (0.0499 g, 0.2 mmol), (±)-1c (0.2165 g, 1 mmol), water (360 μL, d=1.0 g/mL, 0.36 g, 20 mmol), toluene (5 mL), reacted at −5° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2c (0.0687 g, 28%): solid; 94% ee (HPLC conditions: AS-H column, hexane/i-PrOH=98/2, 1.0 mL/min, λ=214 nm, $t_R$ (major)=6.5 min, $t_R$ (minor)=7.8 min); $[α]_D^{26}$=+16.5 (c=1.00, CHCl$_3$). Melting point: 96.8-98.5° C. (measuring directly after solvent evaporates to dryness). $^1$H NMR (400 MHz, CDCl$_3$): δ=7.27-7.20 (m, 1H, Ar—H), 7.20-7.15 (m, 2H, Ar—H), 7.07 (d, J=7.2 Hz, 1H, Ar—H), 2.40-2.28 (m, 5H, CH$_2$ and CH$_3$), 2.18 (s, 3H, CH$_3$), 1.51-1.41 (m, 2H, CH$_2$), 1.41-1.28 (m, 2H, CH$_2$), 0.88 (t, J=7.4 Hz, 3H, CH$_3$); $^{13}$C NMR (100 MHz, CDCl$_3$): δ=212.6, 172.8, 138.1, 134.9, 128.42, 128.37, 126.7, 123.2, 105.2, 101.6, 30.2, 28.3, 22.3, 21.5, 16.4, 13.8; IR (neat): ν=3250-2400 (br), 1932, 1674, 1418, 1276, 1063 cm$^{-1}$; MS (70 eV, EI) m/z (%): 245 (M$^+$+1, 3.90), 244 (M$^+$, 9.06), 157 (100); Anal. Calcd. for C$_{16}$H$_{20}$O$_2$: C, 78.65, H, 8.25; found C, 78.57, H, 8.21.

Operations were conducted by referring to Example 1. PdCl$_2$ (0.0037 g, 0.02 mmol), (R)-L4c (0.0569 g, 0.048 mmol), PPh$_3$ (0.0525 g, 0.2 mmol), (PhO)$_2$PO$_2$H (0.05 g, 0.2 mmol), (±)-1d (0.2175 g, 1 mmol), water (360 μL, d=1.0 g/mL, 0.36 g, 20 mmol), toluene (5 mL), reacted at −5° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2d (0.0909 g, 37%): solid; 90% ee (HPLC conditions: AS-H column, hexane/i-PrOH=98/2, 1.0 mL/min, λ=214 nm, $t_R$(major)=7.9 min, $t_R$(minor)=8.5 min); $[α]_D^{26}$=+15.8 (c=1.00, CHCl$_3$). Melting point: 109.3-111.1° C. (measuring directly after solvent evaporates to dryness). $^1$H NMR (400 MHz, CDCl$_3$): δ=7.26 (d, J=8.0 Hz, 2H, Ar—H), 7.14 (d, J=7.6 Hz, 2H, Ar—H), 2.40-2.25 (m, 5H, CH$_2$ and CH$_3$), 2.17 (s, 3H, CH$_3$), 1.54-1.40 (m, 2H, CH$_2$), 1.40-1.27 (m, 2H, CH$_2$), 0.87 (t, J=7.2 Hz, 3H, CH$_3$); $^{13}$C NMR (100 MHz, CDCl$_3$): δ=212.5, 173.1, 137.4, 132.0, 129.2, 126.0, 105.0, 101.7, 30.2, 28.3, 22.2, 21.1, 16.3, 13.8; IR (neat): ν=3210-2400 (br), 1936, 1673, 1417, 1278, 1066 cm$^{-1}$; MS (70 eV, EI) m/z (%): 245 (M$^+$+1, 10.17), 244 (M$^+$, 6.23), 157 (100); Anal. Calcd. for C$_{16}$H$_{20}$O$_2$: C, 78.65, H, 8.25; found C, 78.65, H, 8.22.

Example 4

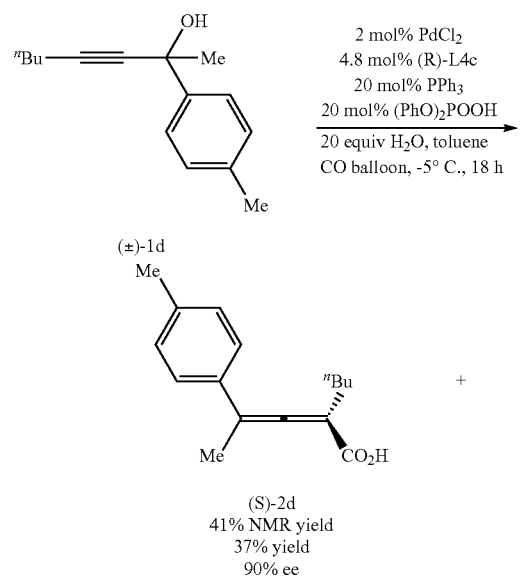

Example 5

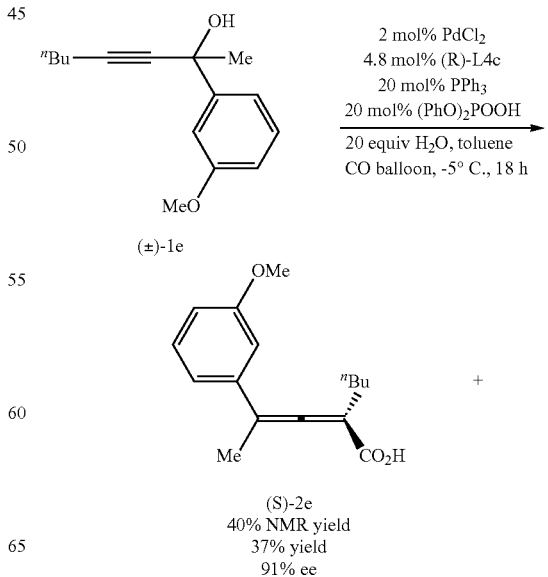

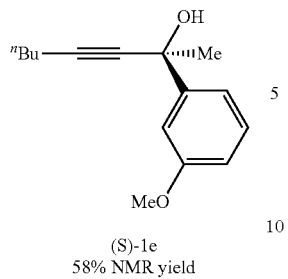

(S)-1e
58% NMR yield

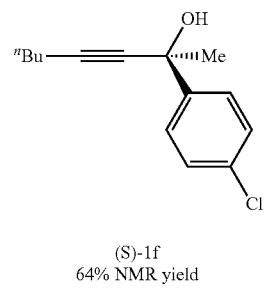

(S)-1f
64% NMR yield

Operations were conducted by referring to Example 1. PdCl$_2$ (0.0036 g, 0.02 mmol), (R)-L4c (0.0566 g, 0.048 mmol), PPh$_3$ (0.0524 g, 0.2 mmol), (PhO)$_2$PO$_2$H (0.0504 g, 0.2 mmol), (±)-1e (0.2324 g, 1 mmol), water (360 μL, d=1.0 g/mL, 0.36 g, 20 mmol), toluene (5 mL), reacted at −5° C. for 18 hours. Flash column chromatography (eluent: petroleum ether (60~90° C.)/ether/dichloromethane=20/1/1) to afford a product: chiral allenic acid (S)-2e (0.0963 g, 37%): solid; 91% ee (HPLC conditions: AS-H column, hexane/i-PrOH=95/5, 1.3 mL/min, λ=214 nm, $t_R$ (major)=4.7 min, $t_R$ (minor)=5.8 min); $[α]_D^{27}$=+16.8 (c=1.11, CHCl$_3$). Melting point: 58.5-60.0° C. (petroleum ether/dichloromethane recrystallization). $^1$H NMR (400 MHz, CDCl$_3$): δ=7.26 (t, J=8.0 Hz, 1H, Ar—H), 7.03-6.88 (m, 2H, Ar—H), 6.80 (dd, J$_1$=8.0 Hz, J$_2$=2.0 Hz, 1H, Ar—H), 3.80 (s, 3H, OCH$_3$), 2.32 (t, J=7.4 Hz, 2H, CH$_2$), 2.18 (s, 3H, CH$_3$), 1.55-1.27 (m, 4H, 2×CH$_2$), 0.88 (t, J=7.4 Hz, 3H, CH$_3$); $^{13}$C NMR (100 MHz, CDCl$_3$): δ=212.6, 172.8, 159.7, 136.5, 129.5, 118.6, 112.8, 112.0, 105.1, 101.8, 55.2, 30.2, 28.3, 22.2, 16.3, 13.2; IR (neat): ν=3200-2410 (br), 1936, 1679, 1465, 1417, 1374, 1320, 1283, 1204, 1175, 1122, 1084, 1047, 1032, 1010 cm$^{-1}$; MS (70 eV, EI) m/z (%): 261 (M$^+$+1, 2.06), 260 (M$^+$, 11.47), 173 (100); HRMS: Calcd for C$_{16}$H$_{20}$O$_3$ (M$^+$): 260.1407; Found: 260.1402.

Example 6

Operations were conducted by referring to Example 1. PdCl$_2$ (0.0036 g, 0.02 mmol), (R)-L4c (0.0564 g, 0.048 mmol), PPh$_3$ (0.053 g, 0.2 mmol), (PhO)$_2$PO$_2$H (0.0505 g, 0.2 mmol), (±)-1f (0.2356 g, 1 mmol), water (360 μL, d=1.0 g/mL, 0.36 g, 20 mmol), toluene (5 mL), reacted at −5° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2f (0.1086 g, 41%): solid; 94% ee (HPLC conditions: AS-H column, hexane/i-PrOH=98/2, 1.0 mL/min, λ=214 nm, $t_R$ (major)=8.4 min, $t_R$ (minor)=10.4 min); $[α]_D^{26}$=+37.8 (c=1.20, CHCl$_3$). Melting point: 110.4-111.7° C. (measuring directly after solvent evaporates to dryness). $^1$H NMR (400 MHz, CDCl$_3$): δ=7.30 (s, 4H, Ar—H), 2.32 (t, J=7.4 Hz, 2H, CH$_2$), 2.16 (s, 3H, CH$_3$), 1.50-1.40 (m, 2H, CH$_2$), 1.40-1.28 (m, 2H, CH$_2$), 0.88 (t, J=7.4 Hz, 3H, CH$_3$); $^{13}$C NMR (100 MHz, CDCl$_3$): δ=212.5, 172.9, 133.6, 133.4, 128.7, 127.3, 104.4, 102.2, 30.2, 28.2, 22.2, 16.3, 13.8; IR (neat): ν=3200-2410 (br), 1936, 1672, 1416, 1281, 1089 cm$^{-1}$; MS (70 eV, EI) m/z (%): 266 (M$^+$($^{37}$Cl), 2.09), 264 (M$^+$($^{35}$Cl), 4.20), 177 (100); Anal. Calcd. for C$_{15}$H$_{17}$ClO$_2$: C, 68.05, H, 6.47; found C, 67.95, H, 6.43.

Example 7

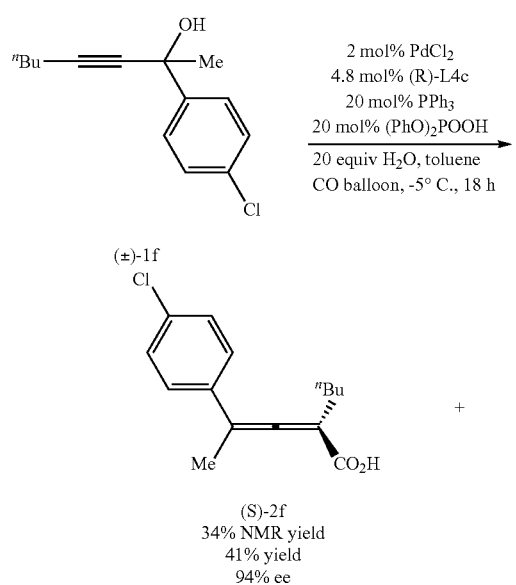

(±)-1f (S)-2f
34% NMR yield
41% yield
94% ee

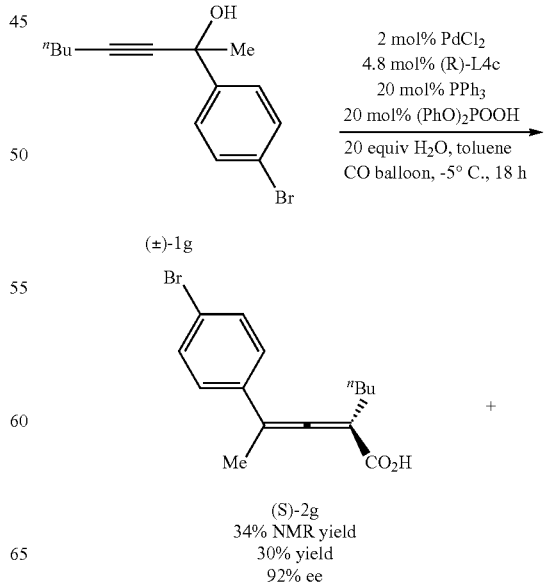

(±)-1g (S)-2g
34% NMR yield
30% yield
92% ee

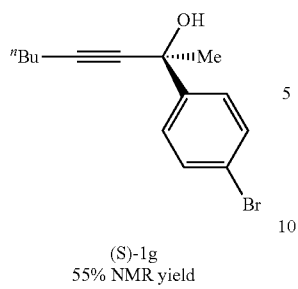

(S)-1g
55% NMR yield

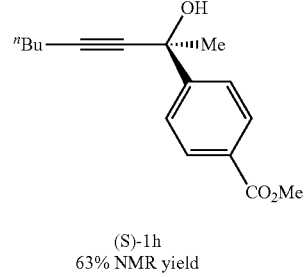

(S)-1h
63% NMR yield

Operations were conducted by referring to Example 1. PdCl$_2$ (0.0036 g, 0.02 mmol), (R)-L4c (0.0578 g, 0.048 mmol), PPh$_3$ (0.0525 g, 0.2 mmol), (PhO)$_2$PO$_2$H (0.05 g, 0.2 mmol), (±)-1g (0.2813 g, 1 mmol), water (360 μL, d=1.0 g/mL, 0.36 g, 20 mmol), toluene (5 mL), reacted at −5° C. for 18 hours. Flash column chromatography (eluent: petroleum ether (60~90° C.)/ether/dichloromethane=30/1/1, petroleum ether (60~90° C.)/ethyl acetate=5/1) to afford a product: chiral allenic acid (S)-2g (0.0928 g, 30%): solid; 92% ee (HPLC conditions: AS-H column, hexane/i-PrOH=95/5, 0.9 mL/min, λ=214 nm, t$_R$ (major)=6.2 min, t$_R$ (minor)=7.7 min); [α]$_D^{26}$=+25.0 (c=1.01, CHCl$_3$). Melting point: 125.1-126.0° C. (petroleum ether/dichloromethane recrystallization). $^1$H NMR (400 MHz, CDCl$_3$): δ=7.46 (d, J=8.4 Hz, 2H, Ar—H), 7.23 (d, J=8.4 Hz, 2H, Ar—H), 2.32 (d, J=7.4 Hz, 2H, CH$_2$), 2.17 (s, 3H, CH$_3$), 1.52-1.29 (m, 4H, 2×CH$_2$), 0.88 (t, J=7.2 Hz, 3H, CH$_3$); $^{13}$C NMR (100 MHz, CDCl$_3$): δ=212.4, 172.2, 134.1, 131.7, 127.6, 121.6, 104.5, 102.2, 30.2, 28.3, 22.2, 16.2, 13.8; IR (neat): ν=3200-2400 (br), 1940, 1685, 1416, 1280, 1075 cm$^{-1}$; MS (70 eV, EI) m/z (%): 310 (M$^+$($^{81}$Br), 1.97), 308 (M$^+$($^{79}$Br), 1.84), 142 (100); HRMS calcd for C$_{15}$H$_{17}$O$_2^{81}$Br [M$^+$]: 310.0387, found: 310.0370.

Example 8

Operations were conducted by referring to Example 1. PdCl$_2$ (0.0037 g, 0.02 mmol), (R)-L4c (0.0571 g, 0.048 mmol), PPh$_3$ (0.0527 g, 0.2 mmol), (PhO)$_2$PO$_2$H (0.05 g, 0.2 mmol), (±)-1h (0.2607 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=20/1/1, petroleum ether (60~90° C.)/ethyl acetate=7/1) to afford a product: chiral allenic acid (S)-2h (0.1013 g, 35%): solid; 97% ee (HPLC conditions: AS-H column, hexane/i-PrOH=90/10, 1.0 mL/min, λ=214 nm, t$_R$(minor)=6.2 min, t$_R$(major)=7.7 min); [α]$_D^{26}$=+22.1 (c=1.00, CHCl$_3$). Melting point: 125.3-127.5° C. (measuring directly after solvent evaporates to dryness). $^1$H NMR (400 MHz, CDCl$_3$): δ=8.00 (d, J=8.4 Hz, 2H, Ar—H), 7.44 (d, J=8.4 Hz, 2H, Ar—H), 3.92 (s, 3H, OCH$_3$), 2.34 (t, J=7.4 Hz, 2H, CH$_2$), 2.21 (s, 3H, CH$_3$), 1.52-1.40 (m, 2H, CH$_2$), 1.40-1.28 (m, 2H, CH$_2$), 0.88 (t, J=7.4 Hz, 3H, CH$_3$); $^{13}$C NMR (100 MHz, CDCl$_3$): δ=213.1, 172.4, 166.8, 139.9, 129.8, 129.0, 125.9, 104.7, 102.3, 52.1, 30.1, 28.2, 22.2, 16.2, 13.8; IR (neat): ν=3250-2400 (br), 1938, 1680, 1423, 1270, 1107 cm$^{-1}$; MS (70 eV, EI) m/z (%): 289 (M$^+$+1, 2.11), 288 (M$^+$, 10.34), 143 (100); Anal. Calcd. for C$_{17}$H$_{20}$O$_4$: C, 70.81, H, 6.99; found C, 70.67, H, 7.13.

Example 9

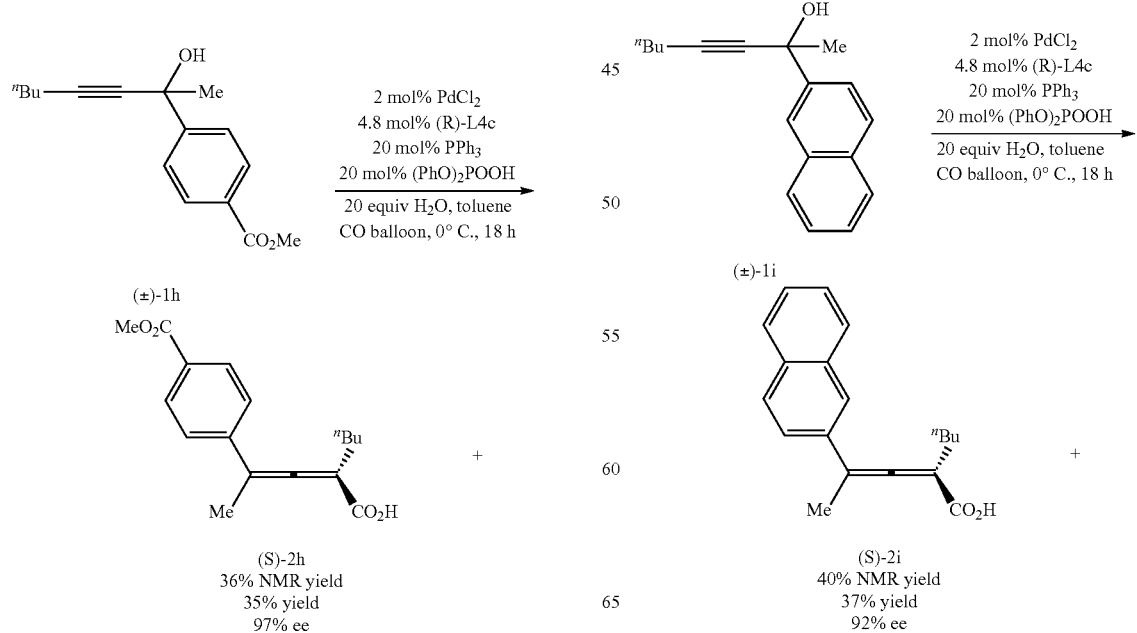

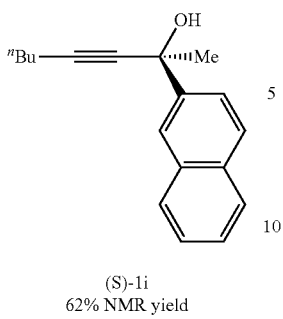

(S)-1i
62% NMR yield

Operations were conducted by referring to Example 1. PdCl$_2$ (0.0035 g, 0.02 mmol), (R)-L4c (0.0578 g, 0.048 mmol), PPh$_3$ (0.0524 g, 0.2 mmol), (PhO)$_2$PO$_2$H (0.05 g, 0.2 mmol), (±)-1i (0.2523 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1-10/1/1) to afford a product: chiral allenic acid (S)-2i (0.1037 g, 37%): solid; 92% ee (HPLC conditions: AS-H column, hexane/i-PrOH=95/5, 1.3 mL/min, λ=214 nm, $t_R$(major)=4.5 min, $t_R$(minor)=5.6 min); $[α]_D^{27}$=−9.2 (c=1.02, CHCl$_3$). Melting point: 137.5-138.4° C. (petroleum ether/ethyl acetate). $^1$H NMR (400 MHz, CDCl$_3$): δ=7.94-7.61 (m, 4H, Ar—H), 7.62-7.30 (m, 3H, Ar—H), 2.60-2.08 (m, 5H, CH$_3$ and CH$_2$), 1.64-1.29 (m, 4H, 2×CH$_2$), 0.88 (t, J=7.0 Hz, 3H, CH$_3$); $^{13}$C NMR (100 MHz, CDCl$_3$): δ=213.2, 172.6, 133.5, 132.8, 132.4, 128.10, 128.06, 127.6, 126.3, 126.1, 124.8, 124.2, 105.5, 102.1, 30.2, 28.4, 22.3, 16.3, 13.8; IR (neat): ν=3200-2410 (br), 1936, 1680, 1412, 1277, 1247 cm$^{-1}$; MS (70 eV, EI) m/z (%): 281 (M$^+$+1, 4.05), 280 (M$^+$, 15.75), 193 (100); Anal. Calcd. for C$_{19}$H$_{20}$O$_2$: C, 81.40, H, 7.19; found C, 81.45, H, 7.20.

Operations were conducted by referring to Example 1. PdCl$_2$ (0.0036 g, 0.02 mmol), (R)-L4c (0.0571 g, 0.048 mmol), PPh$_3$ (0.0524 g, 0.2 mmol), (PhO)$_2$PO$_2$H (0.05 g, 0.2 mmol), (±)-1j (0.2086 g, 1 mmol), water (360 μL, d=1.0 g/mL, 0.36 g, 20 mmol), toluene (5 mL), reacted at −5° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2j (0.1037 g, 37%): solid; 92% ee (HPLC conditions: AS-H column, hexane/i-PrOH=98/2, 1.0 mL/min, λ=214 nm, $t_R$ (major)=10.5 min, $t_R$(minor)=13.2 min); $[α]_D^{27}$=+11.5 (c=1.00, CHCl$_3$). Melting point: 82.6-83.8° C. (measuring directly after solvent evaporates to dryness). $^1$H NMR (400 MHz, CDCl$_3$): δ=7.28 (d, J=4.8 Hz, 1H, one proton from thieny), 7.16 (d, J=2.8 Hz, 1H, one proton from thieny), 7.04 (d, J=4.8 Hz, 1H, one proton from thieny), 2.31 (t, J=7.6 Hz, 2H, CH$_2$), 2.17 (s, 3H, CH$_3$), 1.52-1.41 (m, 2H, CH$_2$), 1.40-1.29 (m, 2H, CH$_2$), 0.88 (t, J=7.2 Hz, 3H, CH$_3$); $^{13}$C NMR (100 MHz, CDCl$_3$): δ=212.8, 172.3, 136.5, 126.3, 125.9, 120.6, 101.4, 101.3, 30.2, 28.4, 22.3, 16.7, 13.8; IR (neat): ν=3200-2410 (br), 1936, 1673, 1417, 1279, 1079 cm$^{-1}$; MS (70 eV, EI) m/z (%): 237 (M$^+$+1, 1.29), 236 (M$^+$, 7.96), 149 (100); Anal. Calcd. for C$_{13}$H$_{16}$O$_2$S: C, 66.07, H, 6.82; found C, 65.93, H, 6.70.

Example 10

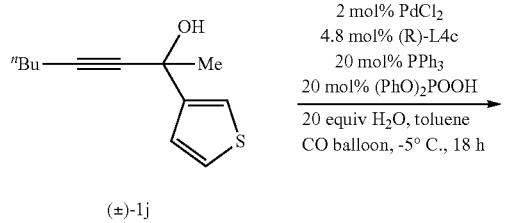

Example 11

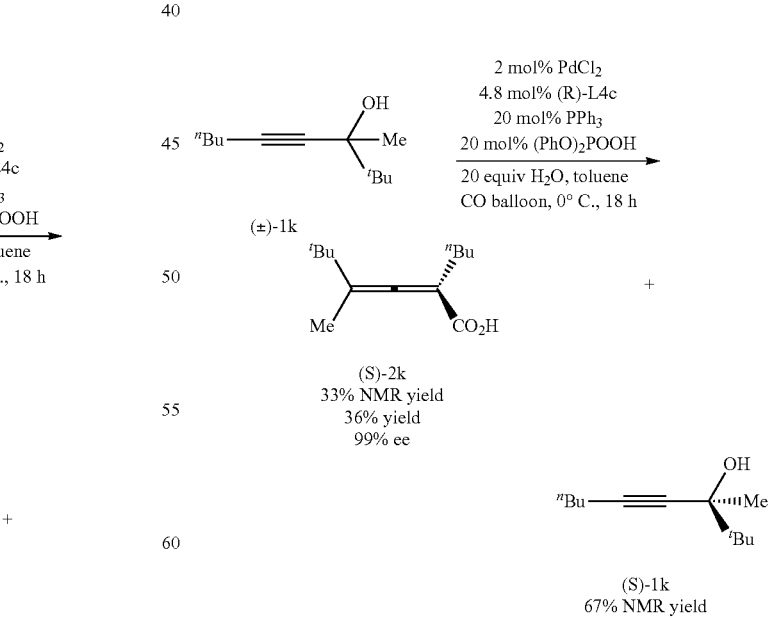

Operations were conducted by referring to Example 1. PdCl$_2$ (0.0036 g, 0.02 mmol), (R)-L4c (0.057 g, 0.048 mmol), PPh$_3$ (0.0524 g, 0.2 mmol), (PhO)$_2$PO$_2$H (0.0501 g, 0.2 mmol), (±)-1k (0.1831 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2k (0.076 g, 36%): oil substance; 99% ee (HPLC conditions: AD-H column, hexane/i-PrOH=98/2, 1.0 mL/min, λ=214 nm, $t_R$ (minor)=6.9 min, $t_R$(major)=7.4 min); $[α]_D^{27}$=+38.5 (c=1.36, CHCl$_3$); $^1$H NMR (400 MHz, CDCl$_3$): δ=2.25-2.13 (m, 2H, CH$_2$), 1.77 (s, 3H, CH$_3$), 1.45-1.29 (m, 4H, 2×CH$_2$), 1.10 (s, 9H, 3×CH$_3$), 0.90 (t, J=7.2 Hz, 3H, CH$_3$); $^{13}$C NMR (100 MHz, CDCl$_3$): δ=208.0, 173.9, 113.0, 99.4, 34.2, 30.3, 28.8, 28.0, 22.3, 14.0, 13.9; IR (neat): ν=3210-2400 (br), 1946, 1669, 1412, 1274, 1240, 1114 cm$^{-1}$; MS (ESI) m/z: 211 (M$^+$H+); HRMS calcd for C$_{13}$H$_{23}$O$_2$ [M+H$^+$]: 211.1693, found: 211.1692.

Example 12

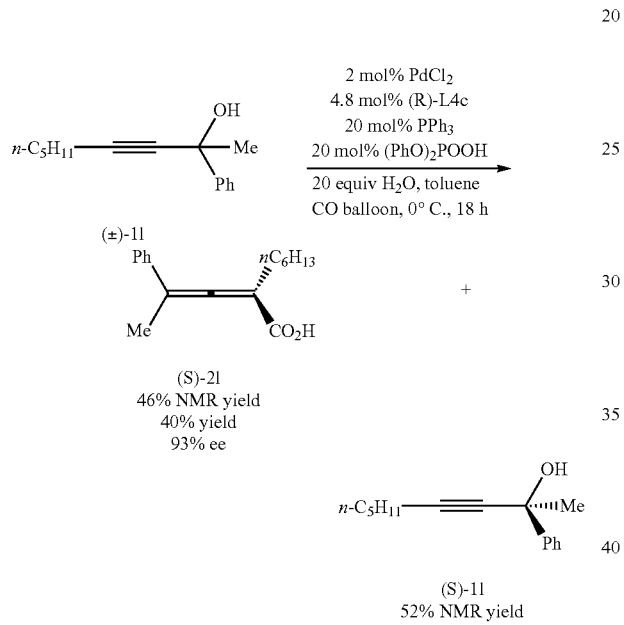

Operations were conducted by referring to Example 1. PdCl$_2$ (0.0036 g, 0.02 mmol), (R)-L4c (0.0569 g, 0.048 mmol), PPh$_3$ (0.0526 g, 0.2 mmol), (PhO)$_2$PO$_2$H (0.0495 g, 0.2 mmol), (±)-1l (0.2175 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2l (0.0984g, 40%): solid; 93% ee (HPLC conditions: AS-H column, hexane/i-PrOH=98/2, 1.0 mL/min, λ=214 nm, $t_R$(major)=7.4 min, $t_R$(minor)=11.5 min); $[α]_D^{27}$=+11.2 (c=1.00, CHCl$_3$). Melting point: 93.2-93.6° C. (measuring directly after solvent evaporates to dryness). $^1$H NMR (400 MHz, CDCl$_3$): δ=7.45-7.29 (m, 4H, Ar—H), 7.29-7.20 (m, 1H, Ar—H), 2.32 (t, J=7.6 Hz, 2H, CH$_2$), 2.19 (s, 3H, CH$_3$), 1.58-1.38 (m, 2H, CH$_2$), 1.36-1.16 (m, 4H, 2×CH$_2$), 0.84 (t, J=6.6 Hz, 3H, CH$_3$); $^{13}$C NMR (100 MHz, CDCl$_3$): δ=212.6, 173.1, 135.0, 128.5, 127.5, 126.0, 105.1, 101.8, 31.3, 28.5, 27.7, 22.4, 16.3, 14.0; IR (neat): ν=3200-2410 (br), 1937, 1675, 1413, 1275, 1064, 1023 cm$^{-1}$; MS (70 eV, EI) m/z (%): 244 (M$^+$, 3.21), 143 (100); Anal. Calcd. for C$_{16}$H$_{20}$O$_2$: C, 78.65, H, 8.25; found C, 78.68, H, 8.38.

Example 13

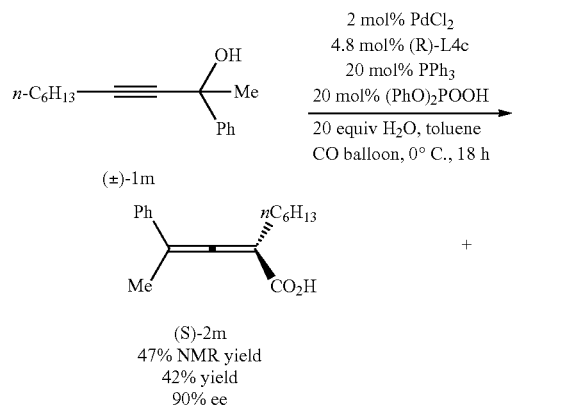

Operations were conducted by referring to Example 1. PdCl$_2$ (0.0037 g, 0.02 mmol), (R)-L4c (0.057 g, 0.048 mmol), PPh$_3$ (0.0524 g, 0.2 mmol), (PhO)$_2$PO$_2$H (0.0501 g, 0.2 mmol), (±)-1m (0.2298 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2m (0.1081 g, 42%): solid; 90% ee (HPLC conditions: AS-H column, hexane/i-PrOH=98/2, 1.0 mL/min, λ=214 nm, $t_R$ (major)=6.6 min, $t_R$ (minor)=9.4 min); $[α]_D^{26}$=+7.4 (c=1.20, CHCl$_3$). Melting point: 76.9-78.1° C. (measuring directly after solvent evaporates to dryness). $^1$H NMR (400 MHz, CDCl$_3$): δ=7.46-7.30 (m, 4H, Ar—H), 7.30-7.21 (m, 1H, Ar—H), 2.32 (t, J=7.4 Hz, 2H, CH$_2$), 2.19 (s, 3H, CH$_3$), 1.53-1.41 (m, 2H, CH$_2$), 1.38-1.11 (m, 6H, 3×CH$_2$), 0.84 (t, J=6.4 Hz, 3H, CH$_3$); $^{13}$C NMR (100 MHz, CDCl$_3$): δ=212.6, 173.0, 135.0, 128.5, 127.5, 126.1, 105.2, 101.8, 31.6, 28.8, 28.6, 28.0, 22.6, 16.3, 14.0; IR (neat): ν=3250-2410 (br), 1936, 1679, 1417, 1272, 1026 cm$^{-1}$; MS (70 eV, EI) m/z (%): 258 (M$^+$, 3.96), 143 (100); Anal. Calcd. for C$_{17}$H$_{22}$O$_2$: C, 79.03, H, 8.58; found C, 78.86, H, 8.62.

Example 14

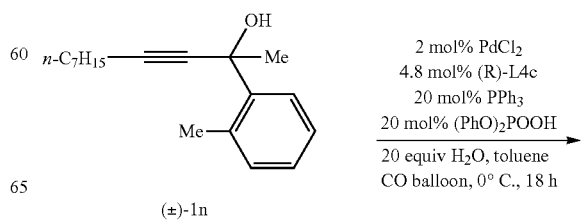

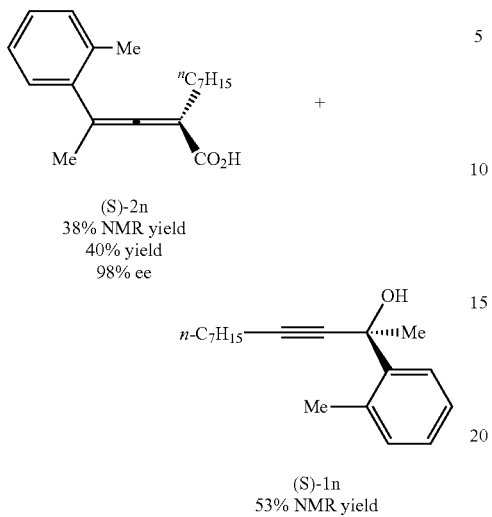

(S)-2n
38% NMR yield
40% yield
98% ee (S)-1n
53% NMR yield (S)-2o
44% NMR yield
41% yield
94% ee (S)-1o
52% NMR yield Operations were conducted by referring to Example 1. PdCl$_2$ (0.0037 g, 0.02 mmol), (R)-L4c (0.0567 g, 0.048 mmol), PPh$_3$ (0.0526 g, 0.2 mmol), (PhO)$_2$PO$_2$H (0.0501 g, 0.2 mmol), (±)-1n (0.2578 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2n (0.1144 g, 40%): oil substance; 98% ee (HPLC conditions: AS-H column, hexane/i-PrOH=98/2, 1.0 mL/min, λ=214 nm, $t_R$(major)=6.0 min, $t_R$(minor)=9.0 min); $[\alpha]_D^{27}$=+69.4 (c=1.34, CHCl$_3$); $^1$H NMR (400 MHz, CDCl$_3$): δ=7.29-7.22 (m, 1H, Ar—H), 7.20-7.12 (m, 3H, Ar—H), 2.40 (s, 3H, CH$_3$), 2.35-2.15 (m, 2H, CH$_2$), 2.13 (s, 3H, CH$_3$), 1.54-1.41 (m, 2H, CH$_2$), 1.35-1.15 (m, 8H, 4×CH$_2$), 0.87 (t, J=6.8 Hz, 3H, CH$_3$); $^{13}$C NMR (100 MHz, CDCl$_3$): δ=210.2, 173.8, 136.2, 136.0, 130.6, 127.9, 127.5, 125.9, 104.5, 98.9, 31.8, 29.11, 29.05, 28.3, 28.0, 22.6, 20.4, 19.9, 14.1; IR (neat): ν=3220-2410 (br), 1948, 1675, 1414, 1274, 1043 cm$^{-1}$; MS (70 eV, EI) m/z (%): 287 (M$^+$+1, 2.48), 286 (M$^+$, 11.23), 143 (100); HRMS calcd for C$_{19}$H$_{26}$O$_2$ [M$^+$]: 286.1933, found: 286.1930.

Example 15

Operations were conducted by referring to Example 1. PdCl$_2$ (0.0037 g, 0.02 mmol), (R)-L4c (0.0569 g, 0.048 mmol), PPh$_3$ (0.0525 g, 0.2 mmol), (PhO)$_2$PO$_2$H (0.05 g, 0.2 mmol), (±)-1o (0.2922 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2o (0.1315 g, 41%): solid; 94% ee (HPLC conditions: AS-H column, hexane/i-PrOH=98/2, 1.0 mL/min, λ=214 nm, $t_R$(major)=6.0 min, $t_R$(minor)=7.8 min); $[\alpha]_D^{27}$=+30.1 (c=1.27, CHCl$_3$). Melting point: 89.2-90.6° C. (measuring directly after solvent evaporates to dryness). $^1$H NMR (400 MHz, CDCl$_3$): δ=7.30 (s, 4H, Ar—H), 2.31 (t, J=7.6 Hz, 2H, CH$_2$), 2.17 (s, 3H, CH$_3$), 1.49-1.40 (m, 2H, CH$_2$), 1.34-1.15 (m, 10H, 5×CH$_2$), 0.86 (t, J=7.0 Hz, 3H, CH$_3$); $^{13}$C NMR (100 MHz, CDCl$_3$): δ=212.5, 173.0, 133.6, 133.4, 128.6, 127.3, 104.4, 102.2, 31.8, 29.3, 29.2, 29.1, 28.5, 28.0, 22.6, 16.2, 14.0; IR (neat): ν=3200-2410 (br), 1938, 1675, 1415, 1274, 1091 cm$^{-1}$; MS (70 eV, EI) m/z (%): 322 (M$^+$($^{37}$Cl), 1.34), 320 (M$^+$($^{35}$Cl), 3.62), 177 (100); Anal. Calcd. for C$_{19}$H$_{25}$ClO$_2$: C, 71.12, H, 7.85; found C, 71.18, H, 7.87.

Example 16

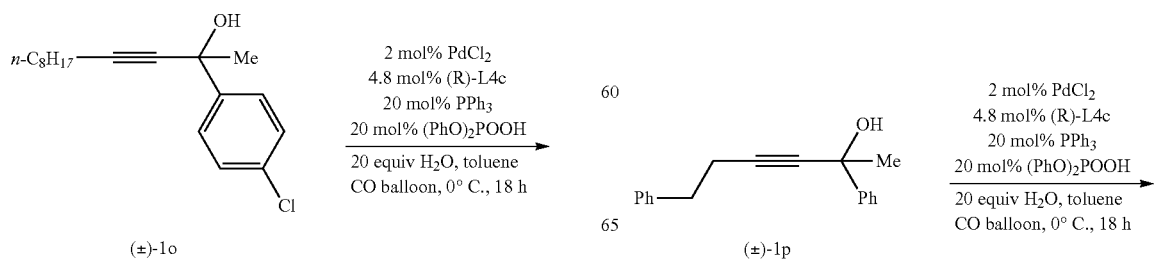

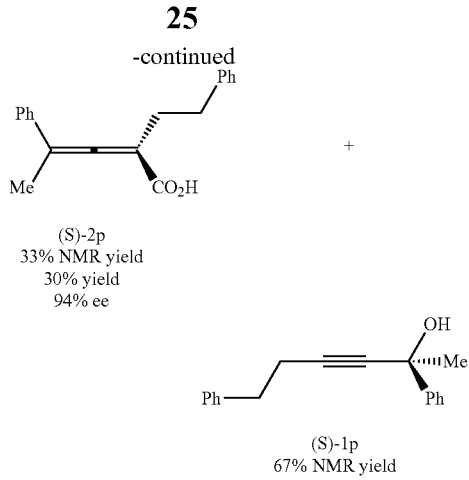

(S)-2p
33% NMR yield
30% yield
94% ee

+

(S)-1p
67% NMR yield

Operations were conducted by referring to Example 1. PdCl$_2$ (0.0037 g, 0.02 mmol), (R)-L4c (0.0566 g, 0.048 mmol), PPh$_3$ (0.0527 g, 0.2 mmol), (PhO)$_2$PO$_2$H (0.0501 g, 0.2 mmol), (±)-1p (0.2504 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=10/1) to afford a product: chiral allenic acid (S)-2p (0.0834 g, 30%): solid; 94% ee (HPLC conditions: AS-H column, hexane/i-PrOH=98/2, 1.0 mL/min, λ=214 nm, $t_R$(major)=13.7 min, $t_R$(minor)=24.1 min); $[α]_D^{25}$=−23.3 (c=1.00, CHCl$_3$). Melting point: 87.4-89.1° C. (measuring directly after solvent evaporates to dryness). $^1$H NMR (400 MHz, CDCl$_3$): δ=7.33-7.20 (m, 7H, Ar—H), 7.19-7.12 (m, 3H, Ar—H), 2.83 (t, J=7.6 Hz, 2H, CH$_2$), 2.76-2.57 (m, 2H, CH$_2$), 2.02 (s, 3H, CH$_3$); $^{13}$C NMR (100 MHz, CDCl$_3$): δ=212.9, 172.6, 141.1, 134.7, 128.5, 128.3, 127.6, 126.1, 125.9, 105.5, 100.7, 34.1, 30.3, 16.1; IR (neat): ν=3200-2410 (br), 1934, 1676, 1417, 1279, 1253, 1065 cm$^{-1}$; MS (70 eV, EI) m/z (%): 279 (M$^+$+1, 1.97), 278 (M$^+$, 9.71), 91 (100); Anal. Calcd. for C$_{19}$H$_{18}$O$_2$: C, 81.99, H, 6.52; found C, 82.12, H, 6.39.

Example 17

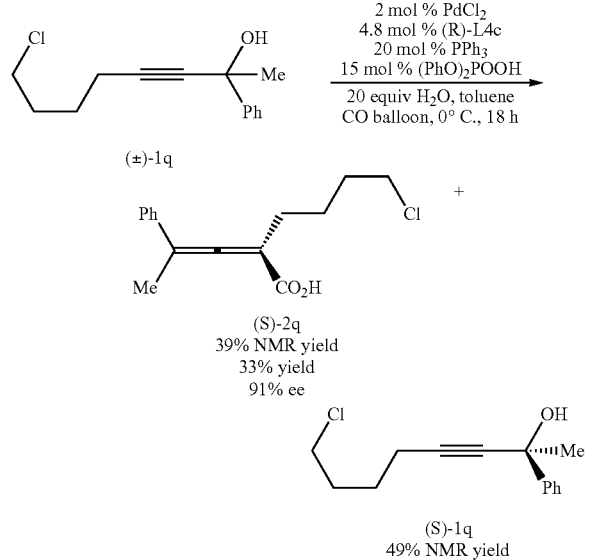

(S)-2q
39% NMR yield
33% yield
91% ee (S)-1q
49% NMR yield

Operations were conducted by referring to Example 1. PdCl$_2$ (0.0037 g, 0.02 mmol), (R)-L4c (0.0571 g, 0.048 mmol), PPh$_3$ (0.0525 g, 0.2 mmol), (PhO)$_2$PO$_2$H (0.0375 g, 0.15 mmol), (±)-1q (0.2356 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=10/1) to afford a product: chiral allenic acid (S)-2q (0.0871 g, 33%): solid; 91% ee (HPLC conditions: AS-H column, hexane/i-PrOH=95/5, 1.3 mL/min, λ=214 nm, $t_R$(major)=5.8 min, $t_R$(minor)=7.4 min); $[α]_D^{27}$=−4.1 (c=1.00, CHCl$_3$). Melting point: 70.7-72.7° C. (measuring directly after solvent evaporates to dryness). $^1$H NMR (400 MHz, CDCl$_3$): δ=7.45-7.30 (m, 4H, Ar—H), 7.30-7.22 (m, 1H, Ar—H), 3.50 (t, J=6.6 Hz, 2H, CH$_2$), 2.36 (t, J=7.6 Hz, 2H, CH$_2$), 2.20 (s, 3H, CH$_3$), 1.87-1.73 (m, 2H, CH$_2$), 1.72-1.55 (m, 2H, CH$_2$); $^{13}$C NMR (100 MHz, CDCl$_3$): δ=212.6, 172.8, 134.7, 128.6, 127.7, 126.1, 105.7, 101.1, 44.6, 32.0, 27.8, 25.3, 16.3; IR (neat): ν=3300-2300 (br), 1933, 1672, 1418, 1272, 1101, 1059, 1015 cm$^{-1}$; MS (70 eV, EI) m/z (%): 266 (M$^+$($^{37}$Cl), 2.35), 264 (M$^+$($^{35}$Cl), 7.78), 143 (100); Anal. Calcd. for C$_{15}$H$_{17}$ClO$_2$: C, 68.05, H, 6.47; found C, 67.77, H, 6.59.

Example 18

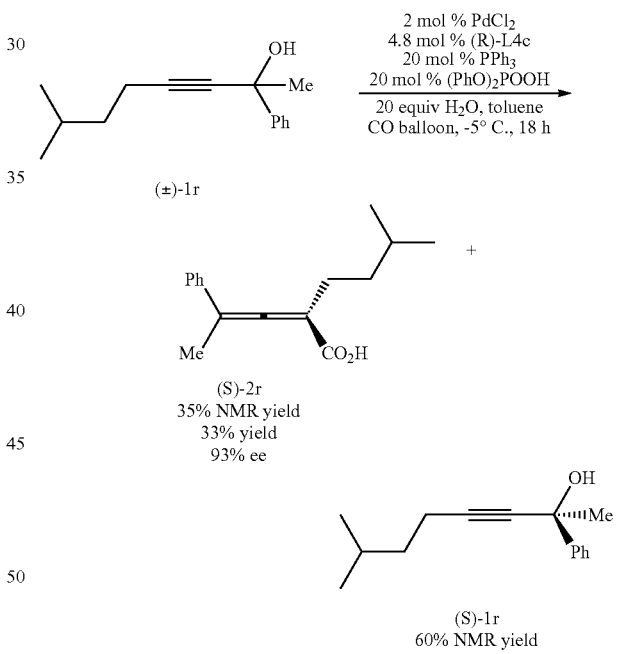

(S)-2r
35% NMR yield
33% yield
93% ee (S)-1r
60% NMR yield

Operations were conducted by referring to Example 1. PdCl$_2$ (0.0037 g, 0.02 mmol), (R)-L4c (0.057 g, 0.048 mmol), PPh$_3$ (0.0526 g, 0.2 mmol), (PhO)$_2$PO$_2$H (0.0501 g, 0.2 mmol), (±)-1r (0.2166 g, 1 mmol), water (360 μL, d=1.0 g/mL, 0.36 g, 20 mmol), toluene (5 mL), reacted at −5° C. for 18 hours. Flash column chromatography (eluent: petroleum ether (60~90° C.)/ether/dichloromethane=30/1/1, petroleum ether (60~90° C.)/ethyl acetate=10/1) to afford a product: chiral allenic acid (S)-2r (0.0808 g, 33%): solid; 93% ee (HPLC conditions: AS-H column, hexane/i-PrOH=98/2, 1.0 mL/min, λ=214 nm, $t_R$ (major)=7.1 min, $t_R$ (minor)=9.0 min); $[α]_D^{27}$=+5.5 (c=1.10, CHCl$_3$). Melting point: 75.2-76.7° C. (measuring directly after solvent evaporates to dryness). $^1$H NMR (400 MHz, CDCl$_3$): δ=7.47-7.28 (m, 4H, Ar—H), 7.28-7.18 (m, 1H, Ar—H), 2.33 (t, J=7.8 Hz, 2H, CH$_3$), 2.18 (s, 3H, CH$_3$), 1.65-1.51 (m, 1H, CH), 1.43-1.29 (m, 2H, CH$_2$), 0.87 (t, J=6.2 Hz, 6H, 2×CH$_3$); $^{13}$C NMR (100 MHz, CDCl$_3$): δ=212.5, 173.1, 135.0, 128.5, 127.6, 126.0, 105.2, 102.0, 37.1, 27.6, 26.6, 22.44, 22.40, 16.3; IR (neat): ν=3250-2410 (br), 1936, 1674, 1467, 1418, 1279, 1256, 1066 cm$^{-1}$; MS (70 eV, EI) m/z (%): 244 (M$^+$, 2.72), 143 (100); Anal. Calcd. for C$_{16}$H$_{20}$O$_2$: C, 78.65, H, 8.25; found C, 78.54, H, 8.32.

Example 19

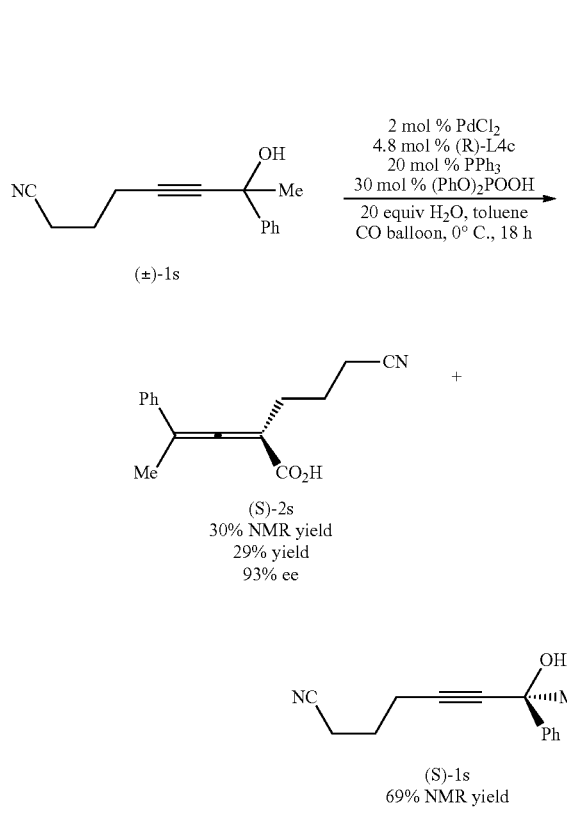

Operations were conducted by referring to Example 1. PdCl$_2$ (0.0036 g, 0.02 mmol), (R)-L4c (0.0569 g, 0.048 mmol), PPh$_3$ (0.0525 g, 0.2 mmol), (PhO)$_2$PO$_2$H (0.075 g, 0.3 mmol), (±)-1s (0.2133 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ethyl acetate=10/1~5/1) to afford a product: chiral allenic acid (S)-2s (0.0702 g, 29%): solid; 93% ee (HPLC conditions: AS-H column, hexane/i-PrOH=90/10, 1.3 mL/min, λ=214 nm, t$_R$(major)=9.9 min, t$_R$(minor)=12.3 min); [α]$_D^{25}$=+23.7 (c=1.10, CHCl$_3$). Melting point: 64.4-65.6° C. (petroleum ether/ether recrystallization). $^1$H NMR (400 MHz, CDCl$_3$): δ=7.39-7.33 (m, 4H, Ar—H), 7.33-7.27 (m, 1H, Ar—H), 2.52-2.44 (m, 2H, CH), 2.35 (t, J=7.2 Hz, 2H, CH$_2$), 2.22 (s, 3H, CH$_3$), 1.89 (quint, J=7.4 Hz, 2H, CH$_2$); $^{13}$C NMR (100 MHz, CDCl$_3$): δ=212.4, 171.9, 134.3, 128.7, 128.0, 126.1, 119.2, 106.3, 99.7, 27.7, 23.9, 16.5, 16.3; IR (neat): ν=3400-2650 (br), 2262, 1939, 1697, 1450, 1394, 1216, 1030 cm$^{-1}$; MS (70 eV, EI) m/z (%): 242 (M$^+$+1, 3.44), 241 (M$^+$, 19.06), 143 (100); Anal. Calcd. for C$_{15}$H$_{15}$NO$_2$: C, 74.67, H, 6.27; found C, 74.43, H, 6.33.

Example 20

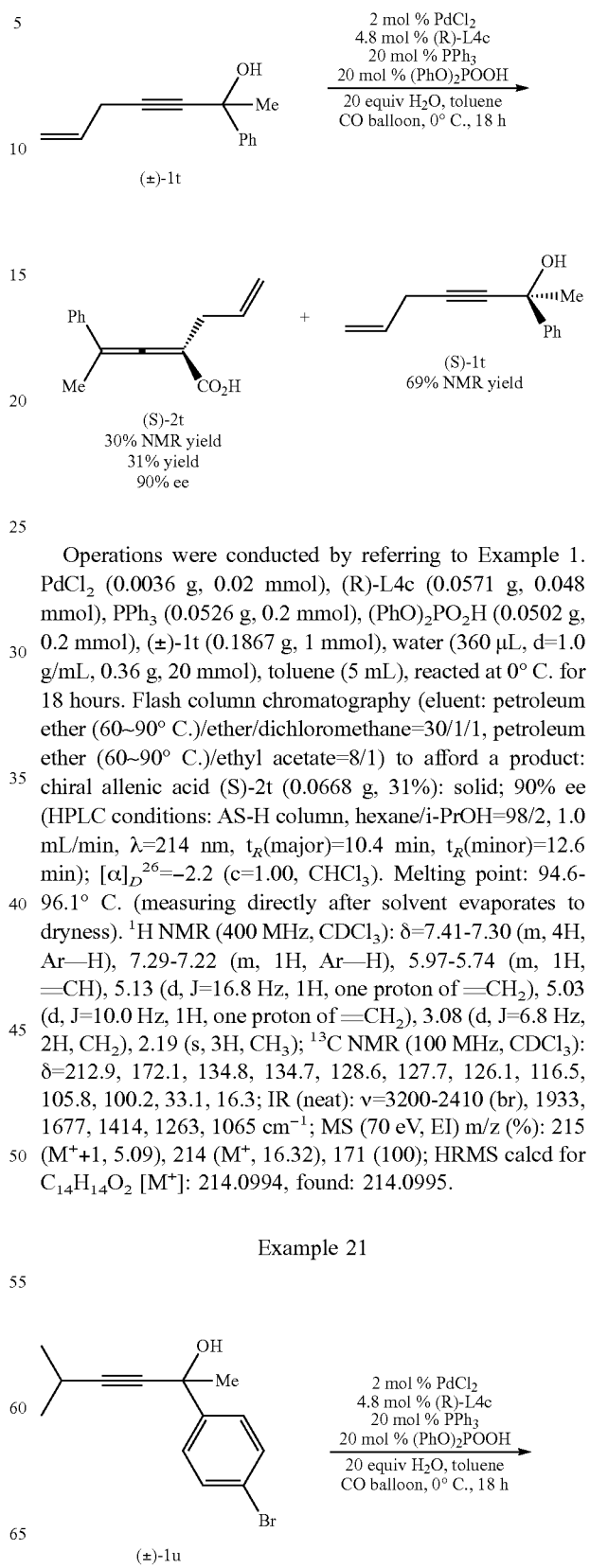

Operations were conducted by referring to Example 1. PdCl$_2$ (0.0036 g, 0.02 mmol), (R)-L4c (0.0571 g, 0.048 mmol), PPh$_3$ (0.0526 g, 0.2 mmol), (PhO)$_2$PO$_2$H (0.0502 g, 0.2 mmol), (±)-1t (0.1867 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2t (0.0668 g, 31%): solid; 90% ee (HPLC conditions: AS-H column, hexane/i-PrOH=98/2, 1.0 mL/min, λ=214 nm, t$_R$(major)=10.4 min, t$_R$(minor)=12.6 min); [α]$_D^{26}$=−2.2 (c=1.00, CHCl$_3$). Melting point: 94.6-96.1° C. (measuring directly after solvent evaporates to dryness). $^1$H NMR (400 MHz, CDCl$_3$): δ=7.41-7.30 (m, 4H, Ar—H), 7.29-7.22 (m, 1H, Ar—H), 5.97-5.74 (m, 1H, =CH), 5.13 (d, J=16.8 Hz, 1H, one proton of =CH$_2$), 5.03 (d, J=10.0 Hz, 1H, one proton of =CH$_2$), 3.08 (d, J=6.8 Hz, 2H, CH$_2$), 2.19 (s, 3H, CH$_3$); $^{13}$C NMR (100 MHz, CDCl$_3$): δ=212.9, 172.1, 134.8, 134.7, 128.6, 127.7, 126.1, 116.5, 105.8, 100.2, 33.1, 16.3; IR (neat): ν=3200-2410 (br), 1933, 1677, 1414, 1263, 1065 cm$^{-1}$; MS (70 eV, EI) m/z (%): 215 (M$^+$+1, 5.09), 214 (M$^+$, 16.32), 171 (100); HRMS calcd for C$_{14}$H$_{14}$O$_2$ [M$^+$]: 214.0994, found: 214.0995.

Example 21

-continued

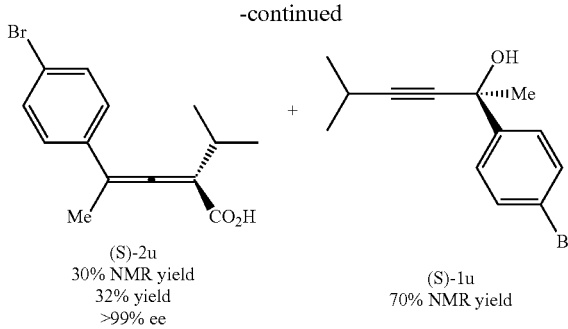

(S)-2u
30% NMR yield
32% yield
>99% ee (S)-1u
70% NMR yield

Operations were conducted by referring to Example 1. PdCl$_2$ (0.0036 g, 0.02 mmol), (R)-L4c (0.057 g, 0.048 mmol), PPh$_3$ (0.0524 g, 0.2 mmol), (PhO)$_2$PO$_2$H (0.0501 g, 0.2 mmol), (±)-1u (0.2672 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2u (0.0947 g, 32%): solid; >99% ee (HPLC conditions: AS-H column, hexane/i-PrOH=98/2, 0.8 mL/min, λ=214 nm, $t_R$(major)=13.6 min); $[α]_D^{26}$=+84.6 (c=1.32, CHCl$_3$). Melting point: 119.2-120.9° C. (petroleum ether/dichloromethane). $^1$H NMR (400 MHz, CDCl$_3$): δ=7.46 (d, J=8.8 Hz, 2H, Ar—H), 7.25 (d, J=8.4 Hz, 2H, Ar—H), 2.80 (heptet, J=6.8 Hz, 1H, CH), 2.18 (s, 3H, CH$_3$), 1.09 (d, J=6.8 Hz, 6H, 2×CH$_3$); $^{13}$C NMR (100 MHz, CDCl$_3$): δ=211.3, 172.4, 134.0, 131.7, 127.4, 121.5, 109.0, 105.8, 28.2, 22.1, 22.1, 16.2; IR (neat): ν=3200-2410 (br), 1938, 1673, 1484, 1412, 1271, 1074 cm$^{-1}$; MS (70 eV, EI) m/z (%): 296 (M$^+$($^{81}$Br), 63.64), 294 (M$^+$($^{79}$Br), 63.57), 155 (100); HRMS calcd for C$_{14}$H$_{15}$$^{79}$BrO$_2$ [M$^+$]: 294.0255, found: 294.0256.

Example 22

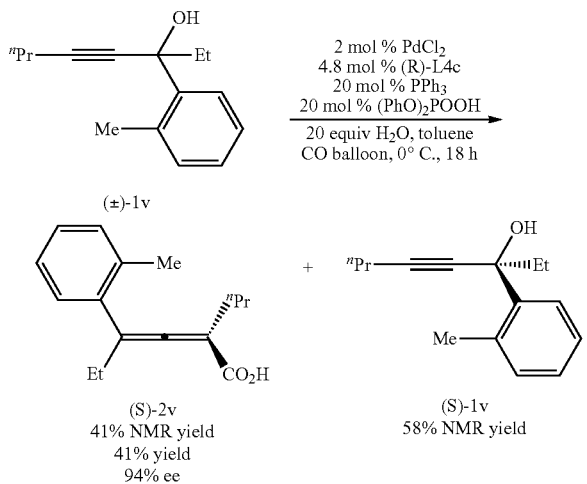

(S)-2v
41% NMR yield
41% yield
94% ee (S)-1v
58% NMR yield

Operations were conducted by referring to Example 1. PdCl$_2$ (0.0036 g, 0.02 mmol), (R)-L4c (0.057 g, 0.048 mmol), PPh$_3$ (0.0526 g, 0.2 mmol), (PhO)$_2$PO$_2$H (0.05 g, 0.2 mmol), (±)-1v (0.2165 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2v (0.1004 g, 41%): oil substance; 94% ee (HPLC conditions: AS-H column, hexane/i-PrOH=98/2, 1.0 mL/min, λ=214 nm, $t_R$(major)=6.3 min, $t_R$(minor)=8.8 min); $[α]_D^{28}$=+103.4 (c=1.10, CHCl$_3$); $^1$H NMR (400 MHz, CDCl$_3$): δ=7.29-7.08 (m, 4H, Ar—H), 2.50-2.32 (m, 5H, CH$_2$ and CH$_3$), 2.32-2.12 (m, 2H, CH$_2$), 1.60-1.42 (m, 2H, CH$_2$), 1.11 (t, J=7.4 Hz, 3H, CH$_3$), 0.93 (t, J=7.4 Hz, 3H, CH$_3$); $^{13}$C NMR (100 MHz, CDCl$_3$): δ=209.2, 174.1, 136.02, 135.97, 130.4, 128.4, 127.5, 125.8, 111.2, 100.6, 30.5, 27.1, 21.4, 20.0, 13.8, 12.2; IR (neat): ν=3200-2410 (br), 1948, 1674, 1414, 1270, 1130 cm$^{-1}$; MS (70 eV, EI) m/z (%): 245 (M$^+$+1, 12.45), 244 (M$^+$, 69.97), 229 (100); HRMS calcd for C$_{16}$H$_{20}$O$_2$ [M$^+$]: 244.1458, found: 244.1455.

Example 23

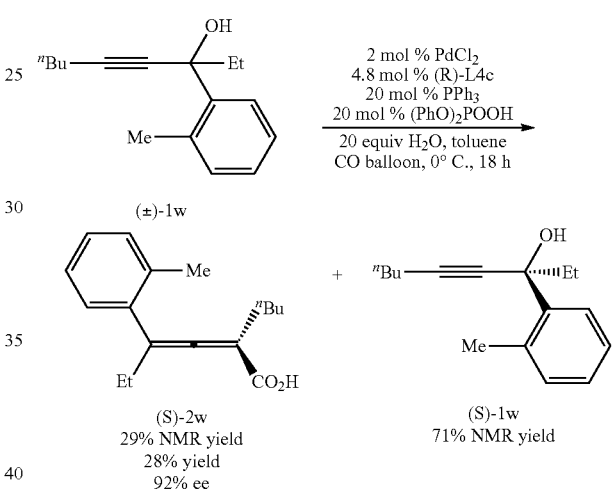

(S)-2w
29% NMR yield
28% yield
92% ee (S)-1w
71% NMR yield

Operations were conducted by referring to Example 1. PdCl$_2$ (0.0037 g, 0.02 mmol), (R)-L4c (0.0571 g, 0.048 mmol), PPh$_3$ (0.0525 g, 0.2 mmol), (PhO)$_2$PO$_2$H (0.05 g, 0.2 mmol), (±)-1w (0.229 g, 1 mmol), water (360 μL, d=1.0 g/mL, 0.36 g, 20 mmol), toluene (5 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2w (0.0723 g, 28%): oil substance; 92% ee (HPLC conditions: AS-H column, hexane/i-PrOH=98/2, 1.0 mL/min, λ=214 nm, $t_R$(major)=5.6 min, $t_R$(minor)=7.7 min); $[α]_D^{27}$=+86.2 (c=1.10, CHCl$_3$); $^1$H NMR (400 MHz, CDCl$_3$): δ=7.26-7.20 (m, 1H, Ar—H), 7.20-7.11 (m, 3H, Ar—H), 2.50-2.15 (m, 7H, 2×CH$_2$ and CH$_3$), 1.54-1.40 (m, 2H, CH$_2$), 1.40-1.28 (m, 2H, CH$_2$), 1.12 (t, J=7.4 Hz, 3H, CH$_3$), 0.90 (t, J=7.2 Hz, 3H, CH$_3$); $^{13}$C NMR (100 MHz, CDCl$_3$): δ=209.1, 174.1, 136.01, 135.96, 130.4, 128.4, 127.5, 125.8, 111.2, 100.7, 30.3, 28.0, 27.1, 22.3, 20.0, 13.8, 12.2; IR (neat): ν=3200-2400 (br), 1949, 1675, 1414, 1275, 1086 cm$^{-1}$; MS (70 eV, EI) m/z (%): 259 (M$^+$+1, 6.05), 258 (M$^+$, 32.38), 129 (100); HRMS calcd for C$_{17}$H$_{22}$O$_2$ [M$^+$]: 258.1620, found: 258.1623.

Example 24

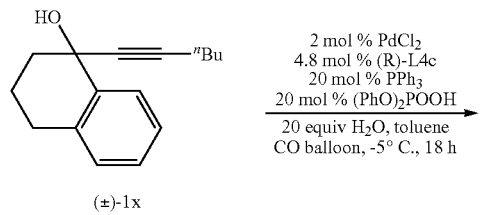

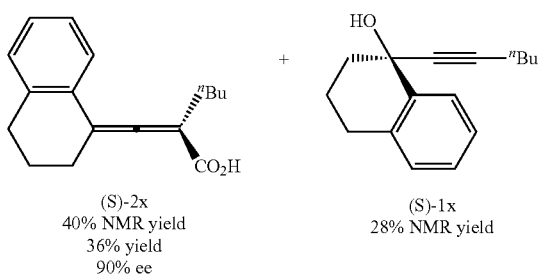

Operations were conducted by referring to Example 1. PdCl$_2$ (0.0036 g, 0.02 mmol), (R)-L4c (0.057 g, 0.048 mmol), PPh$_3$ (0.0527 g, 0.2 mmol), (PhO)$_2$PO$_2$H (0.0501 g, 0.2 mmol), (±)-1x (0.2287 g, 1 mmol), water (360 μL, d=1.0 g/mL, 0.36 g, 20 mmol), toluene (5 mL), reacted at −5° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2x (0.0928 g, 36%): solid; 90% ee (HPLC conditions: AS-H column, hexane/i-PrOH=98/2, 1.0 mL/min, λ=214 nm, $t_R$(major)=9.2 min, $t_R$(minor)=11.2 min). Melting point: 107.7-108.6° C. (measuring directly after solvent evaporates to dryness). $^1$H NMR (400 MHz, CDCl$_3$): δ=7.39-7.29 (m, 1H, Ar—H), 7.17-7.05 (m, 3H, Ar—H), 2.82 (t, J=6.2 Hz, 2H, CH$_2$), 2.72-2.56 (m, 2H, CH$_2$), 2.33 (t, J=7.4 Hz, 2H, CH$_2$), 2.20-1.83 (m, 2H, CH$_2$), 1.52-1.41 (m, 2H, CH$_2$), 1.41-1.28 (m, 2H, CH$_2$), 0.88 (t, J=7.4 Hz, 3H, CH$_3$); $^{13}$C NMR (100 MHz, CDCl$_3$): δ=210.5, 173.0, 136.8, 129.4, 129.3, 127.5, 127.3, 126.2, 106.2, 102.8, 30.2, 29.8, 28.4, 28.0, 22.7, 22.3, 13.8; IR (neat): ν=3200-2400, 1931, 1670, 1418, 1279 cm$^{-1}$; MS (70 eV, EI) m/z (%): 257 (M$^+$+1, 1.91), 256 (M$^+$, 8.77), 169 (100); Anal. Calcd. for C$_{17}$H$_{20}$O$_2$: C, 79.65, H, 7.86; found C, 79.16, H, 7.83.

Example 25

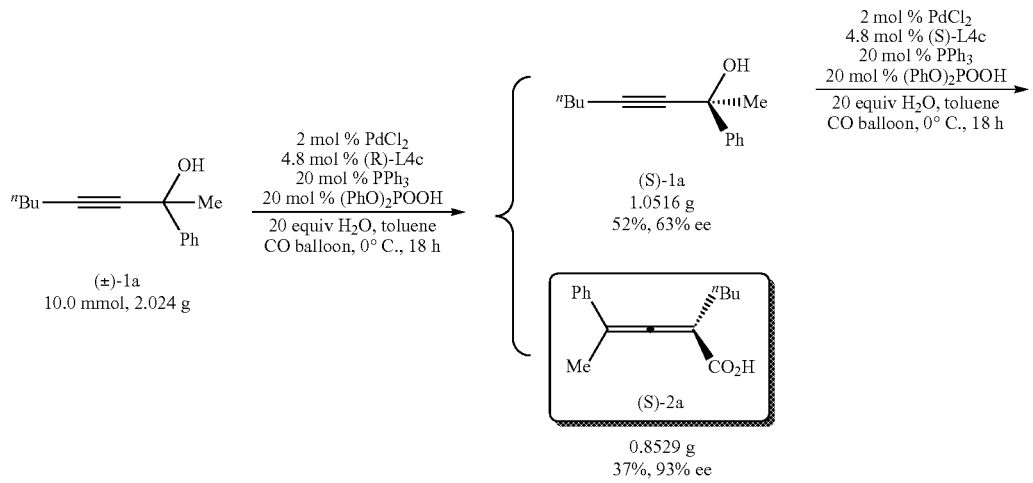

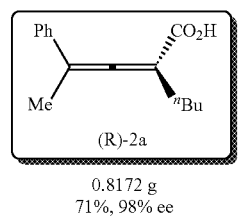

PdCl$_2$ (0.0356 g, 0.2 mmol), chiral diphosphine ligand (R)-L4c (0.5776 g, 0.48 mmol), monophosphine ligand PPh$_3$ (0.5242 g, 2 mmol), and (PhO)$_2$PO$_2$H (0.5006 g, 2 mmol) were added to a dried Schlenk reaction tube. The reaction tube was then plugged with a rubber stopper, and then connected with the vacuum pump, and replaced the argon three times under the argon atmosphere. And under the protection of the argon, tertiary propargyl alcohol (±)-1a (2.0240 g, 10 mmol), toluene (30 mL), water (3.6041 g, 200 mmol) and toluene (20 ml) were added. After closed the argon, freezed the reaction tube in a liquid nitrogen bath for 15 minutes, inserted carbon monoxide balloon (about 2 liters), replaced carbon monoxide under the atmosphere of carbon monoxide three times, then removed the liquid nitrogen bath. When the reaction system returns to room temperature and melted into liquid, put the reaction tube in the preset 0° C. low-temperature bath and stirred for 18 hours. The reaction tube was taken out of the low-temperature bath, and returned to the room temperature and added H$_2$O$_2$ (400 μL, d=1.13 g/mL, 30 wt. % in H$_2$O, 0.135 g, 4 mmol), stirred at the room temperature for 30 minutes. The reaction solution was diluted with ethyl acetate (50 mL), the mixture solution is filtered with silica gel short column (3 cm), and then washed with ethyl acetate (100 mL), concentrated, and subjected to the flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.8259 g, 37%) and (S)-1a (1.0516 g, 52%).

(S)-2a: 93% ee (HPLC conditions: AS-H column, hexane/i-PrOH=98/2, 1.0 mL/min, λ=214 nm, t$_R$(major)=8.5 min, t$_R$(minor)=10.7 min). $^1$H NMR (400 MHz, CDCl$_3$): δ=7.45-7.29 (m, 4H, Ar—H), 7.29-7.17 (m, 1H, Ar—H), 2.32 (t, J=7.4 Hz, 2H, CH$_2$), 2.19 (s, 3H, CH$_3$), 1.54-1.40 (m, 2H, CH$_2$), 1.40-1.27 (m, 2H, CH$_2$), 0.88 (t, J=7.4 Hz, 3H, CH$_3$); $^{13}$C NMR (100 MHz, CDCl$_3$): δ=212.5, 172.8, 135.0, 128.5, 127.5, 126.1, 105.2, 101.8, 30.2, 28.3, 22.3, 16.3, 13.8.

(S)-1a: 63% ee (HPLC conditions: AS-H column, hexane/i-PrOH=98/2, 1.0 mL/min, λ=214 nm, t$_R$(minor)=7.2 min, t$_R$(major)=11.9 min). $^1$H NMR (400 MHz, CDCl$_3$): δ=7.64 (d, J=7.2 Hz, 2H, Ar—H), 7.32 (t, J=7.6 Hz, 2H, Ar—H), 7.28-7.20 (m, 1H, Ar—H), 2.64 (s, 1H, OH), 2.25 (t, J=7.0 Hz, 2H, CH$_2$), 1.72 (s, 3H, CH$_3$), 1.58-1.48 (m, 2H, CH$_2$), 1.48-1.34 (m, 2H, CH$_2$), 0.91 (t, J=7.2 Hz, 3H, CH$_3$).

Operations were conducted by referring to Example 25. PdCl$_2$ (0.0177 g, 0.1 mmol), (R)-L4c (0.2896 g, 0.24 mmol), PPh$_3$ (0.2624 g, 1 mmol), (PhO)$_2$PO$_2$H (0.2501 g, 1 mmol), (S)-1a (1.0109 g, 5 mmol), water (1.8052 g, 100 mmol), toluene (25 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (R)-2a (0.8172 g, 71%): solid; 98% ee (HPLC conditions: AS-H column, hexane/i-PrOH=98/2, 1.0 mL/min, λ=214 nm, t$_R$(minor)=8.1 min, t$_R$(major)=9.8 min); [α]$_D^{28}$=−26.2 (c=0.90, CHCl$_3$). Melting point: 92.2-93.3° C. (measuring directly after solvent evaporates to dryness). $^1$H NMR (400 MHz, CDCl$_3$): δ=7.44-7.29 (m, 4H, Ar—H), 7.29-7.20 (m, 1H, Ar—H), 2.32 (t, J=7.6 Hz, 2H, CH$_2$), 2.19 (s, 3H, CH$_3$), 1.54-1.41 (m, 2H, CH$_2$), 1.41-1.26 (m, 2H, CH$_2$), 0.88 (t, J=7.4 Hz, 3H, CH$_3$); $^{13}$C NMR (100 MHz, CDCl$_3$): δ=212.5, 172.8, 135.0, 128.5, 127.6, 126.1, 105.2, 101.8, 30.2, 28.3, 22.3, 16.3, 13.8; IR (neat): ν=3200-2410 (br), 1936, 1678, 1446, 1280, 1066 cm$^{-1}$; MS (70 eV, EI) m/z (%): 230 (M$^+$, 2.74), 143 (100); HRMS calcd for C$_{15}$H$_{18}$O$_2$ [M$^+$]: 230.1301, found: 230.1295.

Example 26

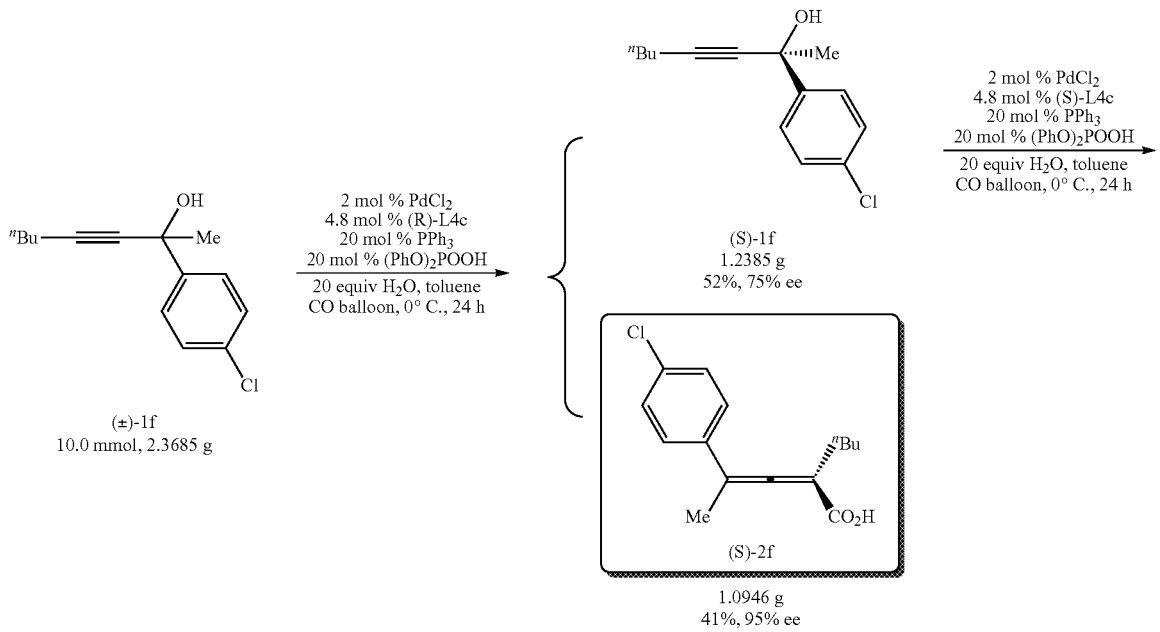

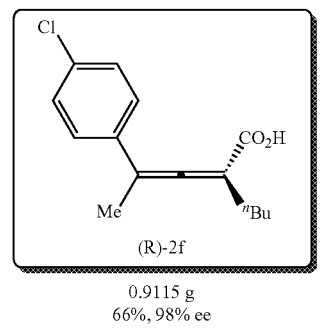

0.9115 g
66%, 98% ee

Operations were conducted by referring to Example 25. PdCl$_2$ (0.0358 g, 0.2 mmol), (R)-L4c (0.5779 g, 0.48 mmol), PPh$_3$ (0.5253 g, 2 mmol), (PhO)$_2$PO$_2$H (0.5005 g, 2 mmol), (±)-1f (2.3685 g, 10 mmol), water (3.6031 g, 200 mmol), toluene (50 mL), reacted at 0° C. for 24 hours. Flash column chromatography (eluent: petroleum ether (60~90° C.)/ether/dichloromethane=30/1/1, petroleum ether (60~90° C.)/ethyl acetate=5/1) to afford products: chiral allenic acid (S)-2f (1.0946 g, 41%) and (S)-1f (1.2385 g, 52%).

(S)-2f: 95% ee (HPLC conditions: AS-H column, hexane/i-PrOH=98/2, 1.0 mL/min, λ=214 nm, t$_R$(major)=8.6 min, t$_R$(minor)=9.6 min). $^1$H NMR (400 MHz, CDCl$_3$): δ=7.29 (s, 4H, Ar—H), 2.32 (t, J=7.6 Hz, 2H, CH$_2$), 2.16 (s, 3H, CH$_3$), 1.50-1.40 (m, 2H, CH$_2$), 1.40-1.28 (m, 2H, CH$_2$), 0.87 (t, J=7.2 Hz, 3H, CH$_3$); $^{13}$C NMR (100 MHz, CDCl$_3$): δ=212.5, 172.9, 133.6, 133.4, 128.7, 127.3, 104.4, 102.2, 30.2, 28.2, 22.2, 16.3, 13.8.

(S)-1f: 75% ee (HPLC conditions: AS-H column, hexane/i-PrOH=98/2, 1.0 mL/min, λ=214 nm, t$_R$ (minor)=7.3 min, t$_R$(major)=10.1 min). $^1$H NMR (400 MHz, CDCl$_3$): δ=7.58 (d, J=8.4 Hz, 2H, Ar—H), 7.31 (d, J=8.4 Hz, 2H, Ar—H), 2.33-2.20 (m, 3H, CH$_2$ and OH), 1.71 (s, 3H, CH$_3$), 1.57-1.48 (m, 2H, CH$_2$), 1.48-1.36 (m, 2H, CH$_2$), 0.93 (t, J=7.4 Hz, 3H, CH$_3$).

Operations were conducted by referring to Example 25. PdCl$_2$ (0.0185 g, 0.1046 mmol), (S)-L4c (0.3025 g, 0.251 mmol), PPh$_3$ (0.2748 g, 1.046 mmol), (PhO)$_2$PO$_2$H (0.2621 g, 1.046 mmol), (5)-1f (1.2385 g, 5.23 mmol), water (1.8883 g, 104.6 mmol), toluene (25 mL), reacted at 0° C. for 24 hours. Flash column chromatography (eluent: petroleum ether (60~90° C.)/ether/dichloromethane=30/1/1, petroleum ether (60~90° C.)/ethyl acetate=5/1) to afford a product: chiral allenic acid (R)-2f (0.9115 g, 66%): solid; 98% ee (HPLC conditions: AS-H column, hexane/i-PrOH=98/2, 1.0 mL/min, λ=214 nm, t$_R$(minor)=8.9 min, t$_R$(major)=9.8 min); [α]$_D^{26}$=−39.7 (c=1.00, CHCl$_3$). Melting point: 108.6-110.0° C. (measuring directly after solvent evaporates to dryness). $^1$H NMR (400 MHz, CDCl$_3$): δ=7.31 (s, 4H, Ar—H), 2.33 (t, J=7.6 Hz, 2H, CH$_2$), 2.17 (s, 3H, CH$_3$), 1.50-1.40 (m, 2H, CH$_2$), 1.40-1.29 (m, 2H, CH$_2$), 0.88 (t, J=7.2 Hz, 3H, CH$_3$); $^{13}$C NMR (100 MHz, CDCl$_3$): δ=212.5, 172.9, 133.6, 133.4, 128.7, 127.3, 104.4, 102.2, 30.1, 28.2, 22.2, 16.2, 13.8; IR (neat): ν=3200-2410 (br), 1940, 1680, 1416, 1280, 1090 cm$^{-1}$; MS (70 eV, EI) m/z (%): 266 (M$^+$($^{37}$C1), 1.42), 264 (M$^+$($^{35}$C1), 3.93), 177 (100); HRMS calcd for C$_{15}$H$_{17}$$^{35}$ClO$_2$ [M$^+$]: 264.0912, found: 264.0913.

Example 27

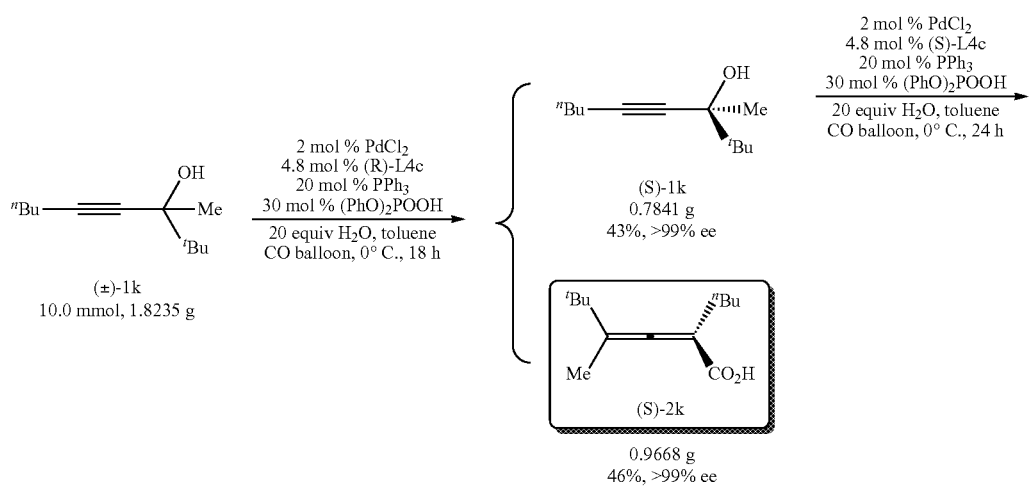

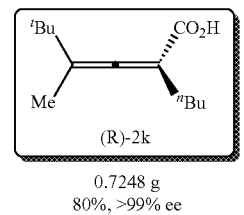

0.7248 g
80%, >99% ee

Operations were conducted by referring to Example 25. PdCl$_2$ (0.0357 g, 0.2 mmol), (R)-L4c (0.5774 g, 0.48 mmol), PPh$_3$ (0.524 g, 2 mmol), (PhO)$_2$PO$_2$H (0.7505 g, 3 mmol), (±)-1k (1.8235 g, 10 mmol), water (3.6009 g, 200 mmol), toluene (50 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford products: chiral allenic acid (S)-2k (0.9668 g, 46%) and (S)-1k (0.7841 g, 43%).

(S)-2k: Melting point: 42.0-44.3° C. (petroleum ether/dichloromethane recrystallization); >99% ee (HPLC conditions: AD-H column, hexane/i-PrOH=98/2, 1.0 mL/min, λ=214 nm, t$_R$ (major)=7.4 min). $^1$H NMR (400 MHz, CDCl$_3$): δ=2.27-2.10 (m, 2H, CH$_2$), 1.77 (s, 3H, CH$_3$), 1.47-1.28 (m, 4H, 2×CH$_2$), 1.10 (s, 9H, 3×CH$_3$), 0.90 (t, J=7.0 Hz, 3H, CH$_3$); $^{13}$C NMR (100 MHz, CDCl$_3$): δ=208.2, 174.5, 112.8, 99.4, 34.2, 30.3, 28.8, 28.0, 22.3, 14.0, 13.9.

(S)-1k: >99% ee (HPLC conditions: IC column, hexane/i-PrOH=98/2, 1.0 mL/min, λ=214 nm, t$_R$(major)=4.7 min). $^1$H NMR (400 MHz, CDCl$_3$): δ=2.20 (t, J=6.8 Hz, 2H, CH$_2$), 1.78 (s, 1H, OH), 1.55-1.34 (m, 7H, 2×CH$_2$ and CH$_3$), 1.03 (s, 9H, 3×CH$_3$), 0.91 (t, J=7.2 Hz, 3H, CH$_3$).

Operations were conducted by referring to Example 25. PdCl$_2$ (0.0152 g, 0.086 mmol), (S)-L4c (0.2489 g, 0.2064 mmol), PPh$_3$ (0.2253 g, 0.86 mmol), (PhO)$_2$PO$_2$H (0.3226 g, 1.29 mmol), (S)-1k (0.7841 g, 4.3 mmol), water (1.5471 g, 86 mmol), toluene (21 mL), reacted at 0° C. for 24 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (R)-2k (0.7248 g, 80%): solid; >99% ee (HPLC conditions: AD-H column, hexane/i-PrOH=98/2, 1.0 mL/min, λ=214 nm, t$_R$ (major)=6.7 min); [α]$_D^{27}$=−37.4 (c=1.00, CHCl$_3$). Melting point: 42.5-44.2° C. (petroleum ether/dichloromethane recrystallization). $^1$H NMR (400 MHz, CDCl$_3$): δ=2.26-2.10 (m, 2H, CH$_2$), 1.77 (s, 3H, CH$_3$), 1.48-1.28 (m, 4H, 2×CH$_2$), 1.10 (s, 9H, 3×CH$_3$), 0.91 (t, J=7.0 Hz, 3H, CH$_3$); $^{13}$C NMR (100 MHz, CDCl$_3$): δ=208.1, 174.5, 112.8, 99.4, 34.2, 30.3, 28.8, 28.0, 22.3, 14.0, 13.9; IR (neat): ν=3210-2410 (br), 1947, 1669, 1413, 1276, 1241, 1113 cm$^{-1}$; MS (ESI) m/z: 211 (M$^+$H+); HRMS calcd for C$_{13}$H$_{23}$O$_2$ [M+H$^+$]: 211.1693, found: 211.1697.

Example 28

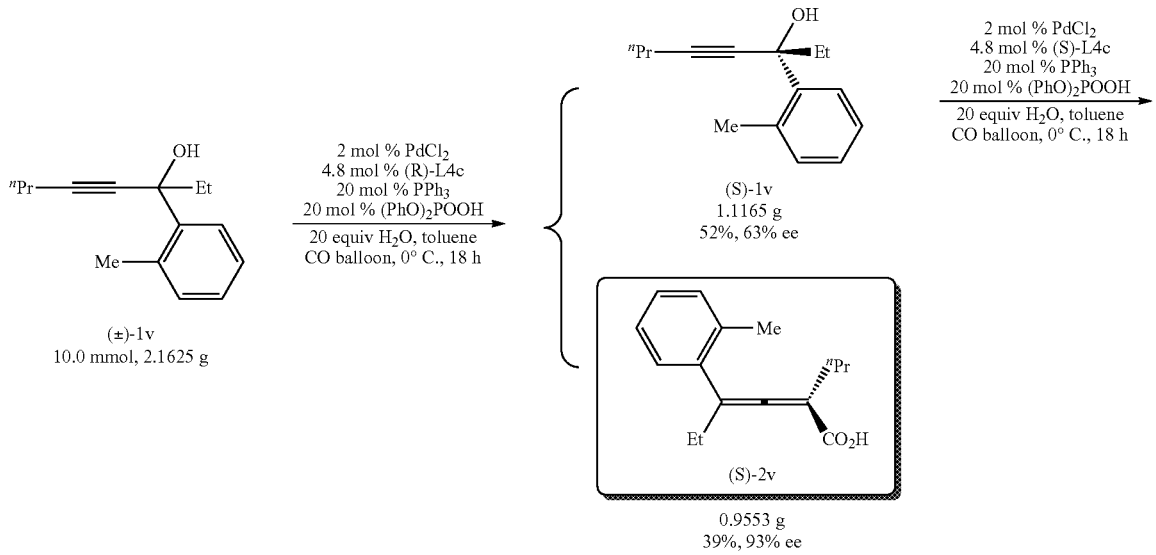

-continued

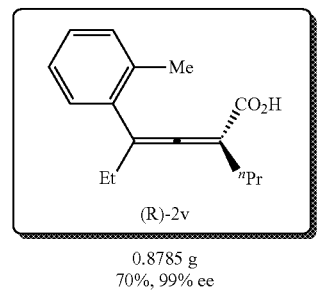

(R)-2v
0.8785 g
70%, 99% ee

Operations were conducted by referring to Example 25. PdCl$_2$ (0.03576 g, 0.2 mmol), (R)-L4c (0.5779 g, 0.48 mmol), PPh$_3$ (0.5247 g, 2 mmol), (PhO)$_2$PO$_2$H (0.5006 g, 2 mmol), (±)-1v (2.1625 g, 10 mmol), water (3.6017 g, 200 mmol), toluene (50 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford products: chiral allenic acid (S)-2v (0.9553 g, 39%) and (S)-1v (1.1165 g, 52%).

(S)-2v: 93% ee (HPLC conditions: AS-H column, hexane/i-PrOH=98/2, 1.0 mL/min, λ=214 nm, t$_R$(major)=6.6 min, t$_R$(minor)=9.2 min). $^1$H NMR (400 MHz, CDCl$_3$): δ=7.27-7.20 (m, 1H, Ar—H), 7.20-7.11 (m, 3H, Ar—H), 2.47-2.32 (m, 5H, CH$_2$ and CH$_3$), 2.32-2.12 (m, 2H, CH$_2$), 1.58-1.44 (m, 2H, CH$_2$), 1.11 (t, J=7.4 Hz, 3H, CH$_3$), 0.93 (t, J=7.4 Hz, 3H, CH$_3$); $^{13}$C NMR (100 MHz, CDCl$_3$): δ=209.2, 174.1, 136.02, 135.97, 130.4, 128.4, 127.5, 125.8, 111.2, 100.6, 30.5, 27.1, 21.4, 20.0, 13.8, 12.2.

(S)-1v (1.1165 g, 52%): 63% ee (HPLC conditions: AS-H column, hexane/i-PrOH=98/2, 1.0 mL/min, λ=214 nm, t$_R$(minor)=5.6 min, t$_R$(major)=7.1 min). $^1$H NMR (400 MHz, CDCl$_3$): δ=7.77-7.68 (m, 1H, Ar—H), 7.23-7.10 (m, 3H, Ar—H), 2.58 (s, 3H, CH$_3$), 2.25 (t, J=7.0 Hz, 2H, CH$_2$), 2.21 (s, 1H, OH), 2.09-1.90 (m, 2H, CH$_2$), 1.60-1.51 (m, 2H, CH$_2$), 1.08-0.91 (m, 6H, 2×CH$_3$).

Operations were conducted by referring to Example 25. PdCl$_2$ (0.0181 g, 0.1032 mmol), (S)-L4c (0.2981 g, 0.248 mmol), PPh$_3$ (0.2704 g, 1.032 mmol), (PhO)$_2$PO$_2$H (0.2581 g, 1.032 mmol), (S)-1v (1.1165 g, 5.16 mmol), water (1.8582 g, 103.2 mmol), toluene (25.8 mL), reacted at 0° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (R)-2v (0.8785 g, 70%): oil substance: 99% ee (HPLC conditions: AS-H column, hexane/i-PrOH=98/2, 1.0 mL/min, λ=214 nm, t$_R$(minor)=5.6 min, t$_R$(major)=6.7 min); [α]$_D^{28}$=−107.5 (c=1.00, CHCl$_3$); $^1$H NMR (400 MHz, CDCl$_3$): δ=7.30-7.08 (m, 4H, Ar—H), 2.48-2.32 (m, 5H, CH$_2$ and CH$_3$), 2.32-2.10 (m, 2H, CH$_2$), 1.61-1.49 (m, 2H, CH$_2$), 1.11 (t, J=7.2 Hz, 3H, CH$_3$), 0.93 (t, J=7.4 Hz, 3H, CH$_3$); $^{13}$C NMR (100 MHz, CDCl$_3$): δ=209.1, 174.1, 136.01, 135.97, 130.4, 128.4, 127.5, 125.8, 111.2, 100.6, 30.5, 27.1, 21.4, 20.0, 13.8, 12.2; IR (neat): ν=3200-2410 (br), 1949, 1675, 1414, 1268, 1121 cm$^{-1}$; MS (70 eV, EI) m/z (%): 245 (M$^+$+1, 9.12), 244 (M$^+$, 45.59), 129 (100); HRMS calcd for C$_{16}$H$_{20}$O$_2$ [M$^+$]: 244.1458, found: 244.1454.

Example 29

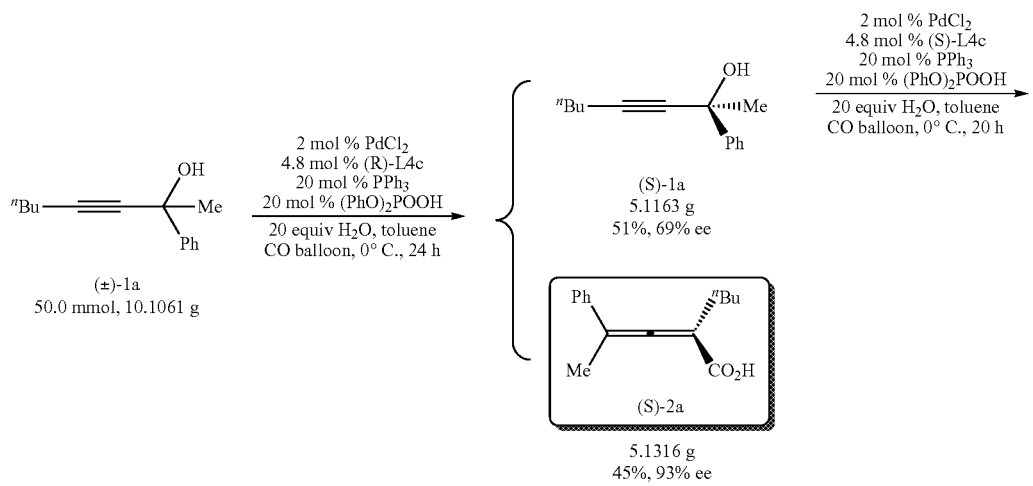

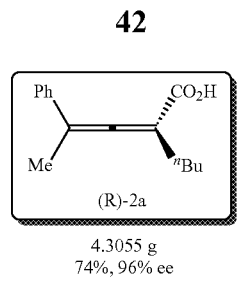

(R)-2a 4.3055 g
74%, 96% ee

Operations were conducted by referring to Example 25. PdCl$_2$ (0.1779 g, 1.0 mmol), (R)-L4c (2.8891 g, 2.4 mmol), PPh$_3$ (2.6243 g, 10 mmol), (PhO)$_2$PO$_2$H (2.5036 g, 10 mmol), (±)-1a (10.1061 g, 50 mmol), water (18.0050 g, 1000 mmol), toluene (250 mL), reacted at 0° C. for 24 hours. Flash column chromatography (eluent: petroleum ether (60~90° C.)/ether/dichloromethane=30/1/1, petroleum ether (60~90° C.)/ethyl acetate=5/1) to afford products: chiral allenic acid (S)-2a (5.1316 g, 45%) and (5)-1a (5.1163 g, 51%).

(S)-2a: 93% ee (HPLC conditions: AS-H column, hexane/i-PrOH=98/2, 1.0 mL/min, λ=214 nm, $t_R$(major)=7.9 min, $t_R$(minor)=9.7 min). $^1$H NMR (400 MHz, CDCl$_3$): δ=7.45-7.28 (m, 4H, Ar—H), 7.27-7.18 (m, 1H, Ar—H), 2.33 (t, J=7.4 Hz, 2H, CH$_2$), 2.18 (s, 3H, CH$_3$), 1.55-1.40 (m, 2H, CH$_2$), 1.40-1.27 (m, 2H, CH$_2$), 0.87 (t, J=7.2 Hz, 3H, CH$_3$); $^{13}$C NMR (100 MHz, CDCl$_3$): δ=212.6, 173.1, 135.0, 128.5, 127.5, 126.1, 105.2, 101.8, 30.2, 28.3, 22.2, 16.3, 13.8.

(S)-1a: 69% ee (HPLC conditions: AS-H column, hexane/i-PrOH=98/2, 1.0 mL/min, λ=214 nm, $t_R$ (minor)=7.1 min, $t_R$ (major)=11.2 min). $^1$H NMR (400 MHz, CDCl$_3$): δ=7.65 (d, J=7.2 Hz, 2H, Ar—H), 7.35 (t, J=7.4 Hz, 2H, Ar—H), 7.31-7.23 (m, 1H, Ar—H), 2.36 (s, 1H, OH), 2.28 (t, J=7.0 Hz, 2H, CH$_2$), 1.74 (s, 3H, CH$_3$), 1.58-1.49 (m, 2H, CH$_2$), 1.49-1.35 (m, 2H, CH$_2$), 0.93 (t, J=7.2 Hz, 3H, CH$_3$).

Operations were conducted by referring to Example 25. PdCl$_2$ (0.09 g, 0.5063 mmol), (5)-L4c (1.4634 g, 1.2151 mmol), PPh$_3$ (1.3287 g, 5.0631 mmol), (PhO)$_2$PO$_2$H (1.268 g, 5.0631 mmol), (5)-1a (5.1163 g, 25.31 mmol), water (9.1162 g, 506.31 mmol), toluene (127 mL), reacted at 0° C. for 20 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (R)-2a (4.3055 g, 74%): solid; 96% ee (HPLC conditions: AS-H column, hexane/i-PrOH=98/2, 1.0 mL/min, λ=214 nm, $t_R$(minor)=8.4 min, $t_R$(major)=10.4 min); $^1$H NMR (400 MHz, CDCl$_3$): δ=7.43-7.29 (m, 4H, Ar—H), 7.29-7.21 (m, 1H, Ar—H), 2.33 (t, J=7.6 Hz, 2H, CH$_2$), 2.19 (s, 3H, CH$_3$), 1.54-1.41 (m, 2H, CH$_2$), 1.41-1.28 (m, 2H, CH$_2$), 0.88 (t, J=7.2 Hz, 3H, CH$_3$); $^{13}$C NMR (100 MHz, CDCl$_3$): δ=212.6, 173.1, 135.0, 128.5, 127.5, 126.0, 105.2, 101.8, 30.2, 28.3, 22.2, 16.3, 13.8.

Example 30

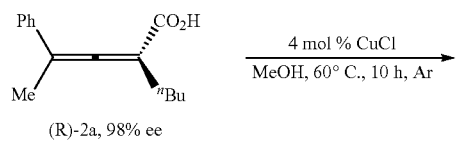

(R)-2a, 98% ee

-continued

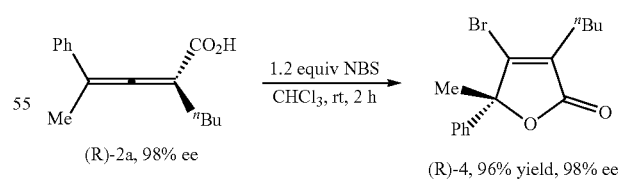

(S)-3, 95% yield, 98% ee (R)-2a (0.1153 g, 0.5 mmol, 98% ee) was added to a dried Schlenk reaction tube, and then took the reaction tube into the glove box and weighed CuCl (0.0023 g, 0.02 mmol), and then took the tube out of the glove box, and added methanol (5 mL) under the protection of argon. The reaction was complete after being stirred at 60° C. oil bath, for 10 h as monitored by thin layer chromatography (TLC). After the methanol was dried, ethyl acetate (5 mL) was added to dissolve the product, quickly filtered by silica gel short column (3 cm) and eluted with ethyl acetate (15 mL), concentrated, and subjected to the flash column chromatography (eluent: petroleum ether (60~90° C.)/ether/dichloromethane=50/1/1) to afford a cyclic product (S)-3 (0.1097 g, 95%): oil substance; 98% ee (HPLC conditions: AD-H column, hexane/i-PrOH=100/1, 0.9 mL/min, λ=214 nm, $t_R$(minor)=26.8 min, $t_R$(major)=29.9 min); $[α]_D^{27}$=−167.8 (c=1.15, CHCl$_3$); $^1$H NMR (400 MHz, CDCl$_3$): δ=7.44-7.26 (m, 5H, Ar—H), 7.23 (s, 1H, =CH), 2.35-2.19 (m, 2H, CH$_2$), 1.78 (s, 3H, CH$_3$), 1.60-1.47 (m, 2H, CH$_2$), 1.43-1.27 (m, 2H, CH$_2$), 0.92 (t, J=7.4 Hz, 3H, CH$_3$); $^{13}$C NMR (100 MHz, CDCl$_3$): δ=173.1, 152.2, 140.1, 132.2, 128.6, 127.9, 124.6, 86.5, 29.3, 26.7, 24.6, 22.1, 13.6; IR (neat): ν=2957, 2929, 2865, 1751, 1448, 1258, 1039 cm$^{-1}$; MS (70 eV, EI) m/z (%): 231 (M$^+$+1, 1.77), 230 (M$^+$, 11.21), 187 (100); HRMS calcd for C$_{15}$H$_{18}$O$_2$ [M$^+$]: 230.1307, found: 230.1304.

Example 31

(R)-2a (0.1151 g, 0.5 mmol, 98% ee), NBS (0.1075 g, 0.6 mmol), chloroform (5 mL) were added to a dried Schlenk reaction tube, and placing the reaction tube at the room temperature. The reaction was complete after being stirred for 2 h as monitored by thin layer chromatography (TLC). After the methanol was dried, subjected to the flash column chromatography (eluent: petroleum ether (60~90° C.)/ether/dichloromethane=50/1/1) to afford a cyclic product (R)-4

(0.1484 g, 96%): solid; 98% ee (HPLC conditions: AD-H column, hexane/i-PrOH=100/1, 0.7 mL/min, λ=214 nm, $t_R$ (minor)=11.6 min, $t_R$ (major)=12.9 min); $[α]_D^{27}$=−149.4 (c=1.30, CHCl$_3$). Melting point: 49.4-49.9° C. (petroleum ether/dichloromethane). $^1$H NMR (400 MHz, CDCl$_3$): δ=7.44-7.29 (m, 5H, Ar—H), 2.36 (t, J=7.6 Hz, 2H, CH$_2$), 1.91 (s, 3H, CH$_3$), 1.65-1.50 (m, 2H, CH$_2$), 1.44-1.26 (m, 2H, CH$_2$), 0.93 (t, J=7.4 Hz, 3H, CH$_3$); $^{13}$C NMR (100 MHz, CDCl$_3$): δ=170.4, 150.4, 137.2, 131.2, 128.8, 128.6, 125.5, 88.1, 29.0, 24.8, 23.8, 22.3, 13.7; IR (neat): ν=2957, 2930, 2862, 1757, 1650, 1448, 1247, 1042 cm$^{-1}$; MS (ESI) m/z (%): 311 (M($^{81}$Br)+H$^+$), 309 (M($^{79}$Br)+H$^+$); Anal. Calcd. for C$_{15}$H$_{17}$BrO$_2$: C, 58.27, H, 5.54; found: C, 58.18, H, 5.56.

Example 32

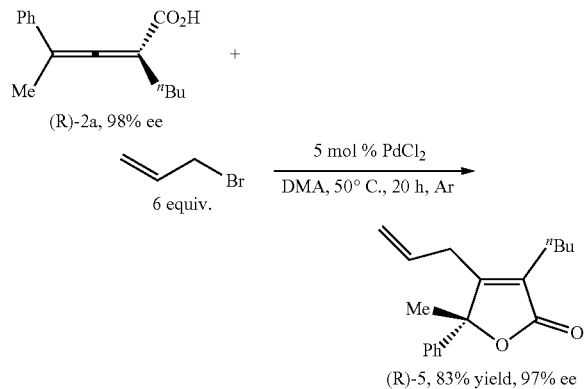

(R)-2a (0.1152 g, 0.5 mmol, 98% ee), PdCl$_2$ (0.0044 g, 0.025 mmol), allyl bromide (260 uL, d=1.398 g/mL, 0.3635 g, 3.0 mmol) were added to a dried Schlenk reaction tube, and then added DMA (N,N-dimethylacetamide) (5 mL) in the protection of argon. The reaction was complete after being stirred at 50° C. oil bath, for 20 h as monitored by thin layer chromatography (TLC). Then the reaction was quenched by water (5 mL), and the aqueous layer was extracted with ether (5 mL×3). The combined organic layer was separated and dried over anhydrous sodium sulfate, then filtered, concentrated, and subjected to the flash silica gel column chromatography (eluent: petroleum ether (60~90° C.)/ether/dichloromethane=50/1/1) to afford a cyclic product (R)-5 (0.1127 g, 83%): oil substance; 97% ee (HPLC conditions: IF column, hexane/i-PrOH=95/5, 1.0 mL/min, λ=214 nm, $t_R$(major)=14.0 min, $t_R$(minor)=15.7 min); $[α]_D^{27}$=−193.6 (c=1.27, CHCl$_3$); $^1$H NMR (400 MHz, CDCl$_3$): δ=7.45-7.23 (m, 5H, Ar—H), 5.58-5.38 (m, 1H, =CH), 5.02 (d, J=4.4 Hz, 1H, one proton of =CH$_2$), 4.98 (s, 1H, one proton of =CH$_2$), 2.99 (dd, J$_1$=15.6 Hz, J$_2$=6.0 Hz, 1H, one proton of CH$_2$), 2.86 (dd, J$_1$=15.6 Hz, J$_2$=7.2 Hz, 1H, one proton of CH$_2$), 2.30 (t, J=7.8 Hz, 2H, CH$_2$), 1.84 (s, 3H, CH$_3$), 1.60-1.48 (m, 2H, CH$_2$), 1.43-1.28 (m, 2H, CH$_2$), 0.93 (t, J=7.2 Hz, 3H, CH$_3$); $^{13}$C NMR (100 MHz, CDCl$_3$): δ=173.8, 164.2, 138.3, 132.3, 128.5, 128.3, 127.5, 125.4, 117.5, 87.8, 30.6, 30.0, 23.4, 23.2, 22.6, 13.7; IR (neat): ν=2954, 2930, 2865, 1748, 1448, 1257, 1207, 1038 cm$^{-1}$; MS (70 eV, EI) m/z (%): 271 (M$^+$+1, 3.32), 270 (M$^+$, 16.82), 229 (100); HRMS calcd for C$_{18}$H$_{22}$O$_2$ [M$^+$]: 270.1620, found: 270.1622.

Example 33

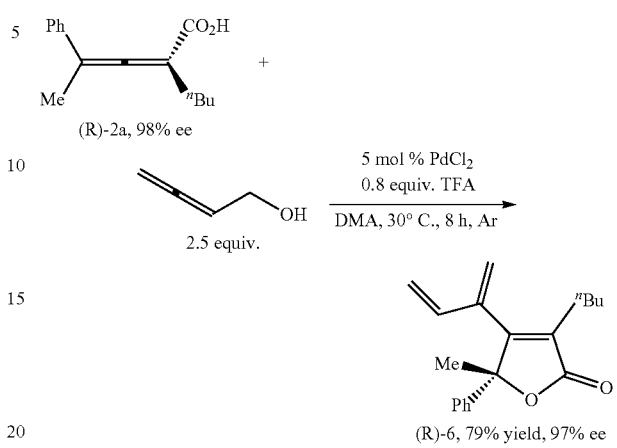

(R)-2a (0.1152 g, 0.5 mmol, 98% ee) and PdCl$_2$ (0.0045 g, 0.025 mmol) were added to a dried Schlenk reaction tube, and then replaced argon three times and added allenic alcohol (0.0875 g, 1.25 mmol), TFA (trifluoroacetic acid) (30 uL, d=1.535 g/mL, 0.0456 g, 0.4 mmol) and DMA (N,N-dimethylacetamide) (5 mL). The reaction was complete after being stirred at 30° C. oil bath, for 8 h as monitored by thin layer chromatography (TLC). Then the reaction was quenched by water (5 mL), and the aqueous layer was extracted with ether (5 mL×3). The combined organic layer was washed with brine and dried over anhydrous sodium sulfate, then filtered, concentrated, and subjected to the flash silica gel column chromatography (eluent: petroleum ether (60~90° C.)/ethyl acetate=50/1) to afford a cyclic product (R)-6 (0.1113 g, 79%): oil substance; 97% ee (HPLC conditions: AD-H column, hexane/i-PrOH=95/5, 1.0 mL/min, λ=214 nm, $t_R$(minor)=6.8 min, $t_R$(major)=7.4 min); $[α]_D^{28}$=−176.7 (c=1.0, CHCl$_3$); $^1$H NMR (400 MHz, CDCl$_3$): δ=7.40-7.17 (m, 5H, Ar—H), 6.28 (dd, J$_1$=17.4 Hz, J$_2$=10.6 Hz, 1H, =CH), 5.27 (s, 1H, one proton of =CH$_2$), 5.00 (d, J=10.4 Hz, 1H, =CH$_2$), 4.74 (d, J=17.6 Hz, 1H, =CH$_2$), 4.47 (s, 1H, one proton of =CH$_2$), 2.26-2.07 (m, 2H, CH$_2$), 1.84 (s, 3H, CH$_3$), 1.58-1.42 (m, 2H, CH$_2$), 1.35-1.21 (m, 2H, CH$_2$), 0.87 (t, J=7.2 Hz, 3H, CH$_3$); $^{13}$C NMR (100 MHz, CDCl$_3$): δ=173.3, 163.3, 138.7, 138.3, 135.8, 128.6, 128.3, 128.1, 125.4, 120.1, 117.2, 88.0, 29.7, 24.3, 24.0, 22.5, 13.7; IR (neat): ν=2955, 2865, 1753, 1450, 1221, 1040 cm$^{-1}$; MS (70 eV, EI) m/z (%): 283 (M$^+$+1, 1.95), 282 (M$^+$, 9.60), 91 (100); HRMS calcd for C$_{19}$H$_{22}$O$_2$ [M$^+$]: 282.1614, found: 282.1614.

Example 34

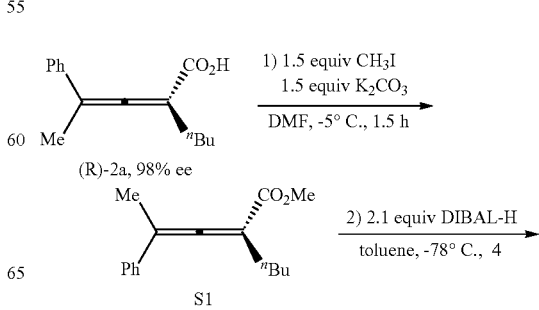

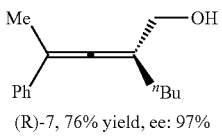

(R)-7, 76% yield, ee: 97%

(R)-2a (0.1151 g, 0.5 mmol, 98% ee), K$_2$CO$_3$ (0.1034 g, 0.75 mmol), DMF (N,N-dimethylformamide) (2.5 mL) were added to a dried Schlenk reaction tube, and putting the reaction tube into −5° C. cold bath and added CH$_3$I (methyl iodide) (47 µL, d=2.28 g/mL, 0.1061 g, 0.75 mmol). The reaction was complete after being stirred at a −5° C. cold bath, for 1.5 h as monitored by thin layer chromatography (TLC). Then the reaction was quenched by water (10 mL), and the aqueous layer was extracted with ether (10 mL×3). The combined organic phases were washed with saturated ammonium chloride solution (10 mL) and brine and dried over anhydrous sodium sulfate, then filtered, concentrated, and subjected to the flash silica gel column chromatography (eluent: petroleum ether (60~90° C.)/ethyl acetate=20/1) to afford oily chiral allenic acid ester S1, and the S1 was directly used in the next reaction.

S1 and toluene (5 mL) were added to a dried Schlenk reaction tube, and putting the reaction tube into −78° C. and added DIBAL-H (diisobutyl-aluminum hydride) (1.05 mL, 1.0 M in Hexane, 1.05 mmol) drop wise. The reaction was complete after being stirred at −78° C., for 4 h as monitored by thin layer chromatography (TLC). Then the reaction was quenched by methanol (5 mL) at −78° C., and took the reaction tube out of cold bath, returned to the room temperature, and added water (10 mL) and 1 mol/L aqueous hydrochloric acid solution (10 mL), and the aqueous layer was extracted with ether (10 mL×3). The combined organic layer was washed with brine (10 mL) once, separated and dried over anhydrous sodium sulfate, then filtered, concentrated, and subjected to the flash silica gel column chromatography (eluent: petroleum ether (60~90° C.)/ethyl acetate=20/1) to afford allenic alcohol (R)-7 (0.0834 g, 77%): oil substance; 97% ee (HPLC conditions: AS-H column, hexane/i-PrOH=98/2, 1.0 mL/min, λ=214 nm, t$_R$ (minor)=8.5 min, t$_R$(major)=11.2 min); [α]$_D^{23}$=+62.0 (c=1.01, CHCl$_3$); $^1$H NMR (400 MHz, CDCl$_3$): δ=7.40 (d, J=7.6 Hz, 2H, Ar—H), 7.31 (t, J=7.6 Hz, 2H, Ar—H), 7.20 (t, J=7.2 Hz, 1H, Ar—H), 4.27-3.99 (m, 2H), 2.22-2.02 (m, 5H, CH$_2$ and CH$_3$), 1.59 (s, 1H, OH), 1.53-1.42 (m, 2H, CH$_2$), 1.42-1.28 (m, 2H, CH$_2$), 0.89 (t, J=7.2 Hz, 3H, CH$_3$); $^{13}$C NMR (100 MHz, CDCl$_3$): δ=199.0, 137.5, 128.3, 126.7, 125.6, 108.0, 104.8, 63.2, 29.9, 29.4, 22.5, 17.4, 13.9; IR (neat): ν=3315, 2954, 2925, 2858, 1948, 1597, 1462, 1067, 1024 cm$^{-1}$; MS (70 eV, EI) m/z (%): 216 (M$^+$, 1.40), 143 (100); HRMS calcd for C$_{15}$H$_{20}$O [M$^+$]: 216.1509, found: 216.1512.

Example 35

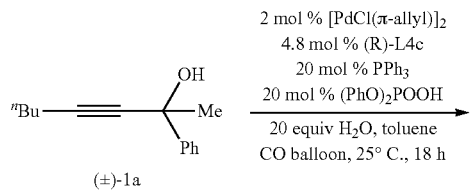

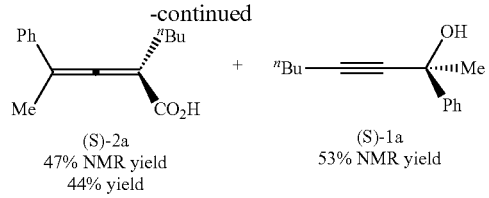

(S)-2a
47% NMR yield
44% yield
85% ee (S)-1a
53% NMR yield

Operations were conducted by referring to Example 1. [PdCl(π-allyl)]$_2$ (0.0015 g, 0.004 mmol), (R)-L4c (0.0148 g, 0.012 mmol), PPh$_3$ (0.0105 g, 0.04 mmol), (PhO)$_2$PO$_2$H (0.001 g, 0.004 mmol), (±)-1a (0.0432 g, 1 mmol), water (72 µL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0167 g, 44%): oil substance; 85% ee (HPLC conditions: AS-H column, hexane/i-PrOH=98/2, 1.0 mL/min, λ=214 nm, t$_R$ (major)=6.4 min, t$_R$ (minor)=9.4 min).

Example 36

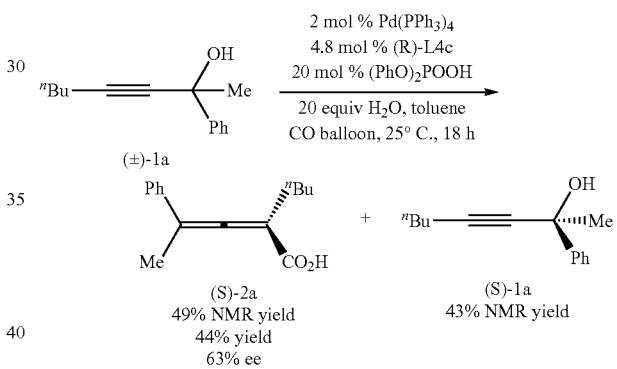

(S)-2a
49% NMR yield
44% yield
63% ee (S)-1a
43% NMR yield

Operations were conducted by referring to Example 1. Pd(PPh$_3$)$_4$ (0.0045 g, 0.004 mmol), (R)-L4c (0.0143 g, 0.012 mmol), (PhO)$_2$PO$_2$H (0.0011 g, 0.004 mmol), (±)-1a (0.0406 g, 0.2 mmol), water (72 µL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0203 g, 44%): oil substance; 63% ee (HPLC conditions: AS-H column, hexane/i-PrOH=98/2, 1.0 mL/min, λ=214 nm, t$_R$(major)=6.4 min, t$_R$(minor)=9.3 min).

Example 37

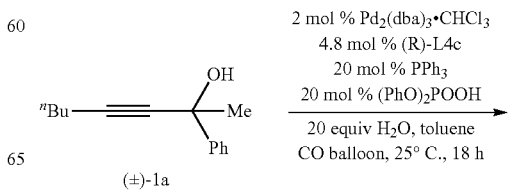

-continued

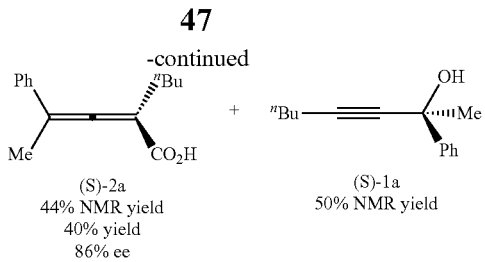

(S)-2a
44% NMR yield
40% yield
86% ee (S)-1a
50% NMR yield

Operations were conducted by referring to Example 1. Pd$_2$(dba)$_3$·CHCl$_3$ (0.0045 g, 0.004 mmol), (R)-L4c (0.0143g, 0.012 mmol), PPh$_3$ (0.0108g, 0.04 mmol), (PhO)$_2$PO$_2$H (0.0012 g, 0.004 mmol), (±)-1a (0.0412 g, 0.2 mmol), water (72 μL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0188 g, 40%): oil substance; 86% ee (HPLC conditions: AS-H column, hexane/i-PrOH=98/2, 1.0 mL/min, λ=214 nm, t$_R$(major)=6.6 min, t$_R$(minor)=9.4 min).

Example 38

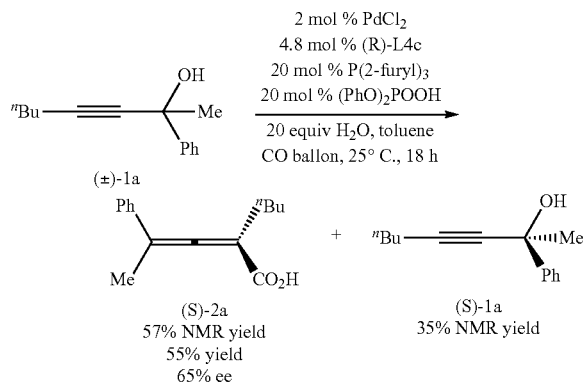

(S)-2a
57% NMR yield
55% yield
65% ee (S)-1a
35% NMR yield

Operations were conducted by referring to Example 1. PdCl$_2$ (0.0015 g, 0.004 mmol), (R)-L4c (0.0146 g, 0.012 mmol), P(2-furyl)$_3$ (0.0096 g, 0.04 mmol), (PhO)$_2$PO$_2$H (0.001 g, 0.004 mmol), (±)-1a (0.0409 g, 1 mmol), water (72 μL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0256 g, 55%): oil substance; 65% ee (HPLC conditions: AS-H column, hexane/i-PrOH=98/2, 1.0 mL/min, λ=214 nm, t$_R$(major)=6.5 min, t$_R$(minor)=9.7 min).

Example 39

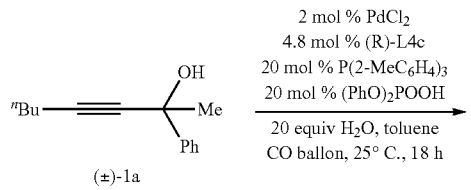

-continued

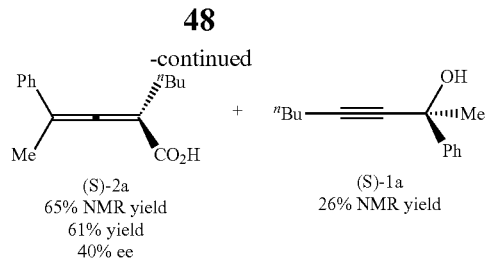

(S)-2a
65% NMR yield
61% yield
40% ee (S)-1a
26% NMR yield

Operations were conducted by referring to Example 1. PdCl$_2$ (0.0016 g, 0.004 mmol), (R)-L4c (0.0143 g, 0.012 mmol), P(2-MeC$_6$H$_4$)$_3$ (0.0122 g, 0.04 mmol), (PhO)$_2$PO$_2$H (0.0011 g, 0.004 mmol), (±)-1a (0.0411 g, 1 mmol), water (72 μL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0286 g, 61%): oil substance; 40% ee (HPLC conditions: AS-H column, hexane/i-PrOH=98/2, 1.0 mL/min, λ=214 nm, t$_R$(major)=6.5 min, t$_R$(minor)=9.7 min).

Example 40

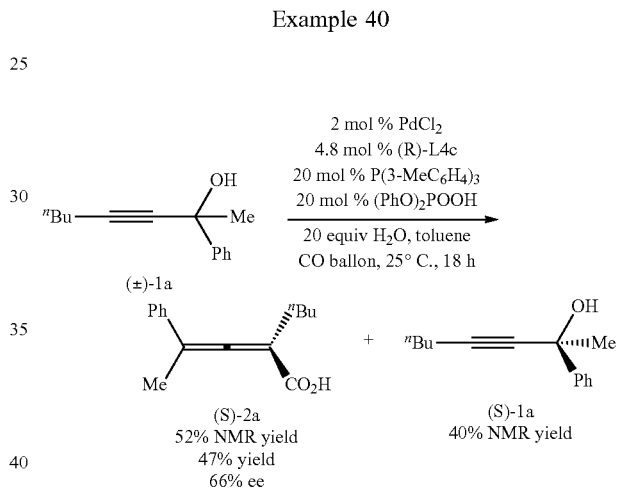

(S)-2a
52% NMR yield
47% yield
66% ee (S)-1a
40% NMR yield

Operations were conducted by referring to Example 1. PdCl$_2$ (0.0015 g, 0.004 mmol), (R)-L4c (0.0148 g, 0.012 mmol), P(3-MeC$_6$H$_4$)$_3$ (0.0129 g, 0.04 mmol), (PhO)$_2$PO$_2$H (0.0011 g, 0.004 mmol), (±)-1a (0.0422 g, 1 mmol), water (72 μL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0226 g, 47%): oil substance; 66% ee (HPLC conditions: AS-H column, hexane/i-PrOH=98/2, 1.0 mL/min, λ=214 nm, t$_R$ (major)=6.4 min, t$_R$ (minor)=9.5 min).

Example 41

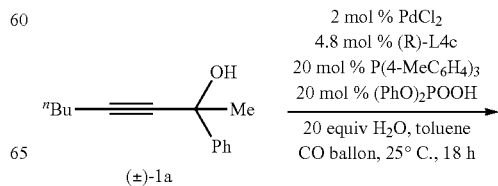

-continued

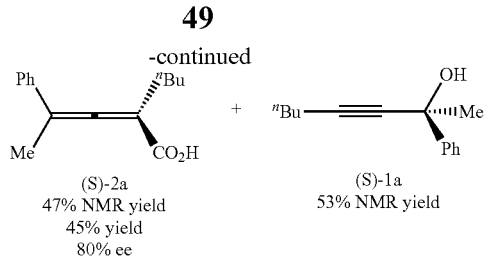

(S)-2a
47% NMR yield
45% yield
80% ee (S)-1a
53% NMR yield

Operations were conducted by referring to Example 1. PdCl$_2$ (0.0015 g, 0.004 mmol), (R)-L4c (0.0145 g, 0.012 mmol), P(4-MeC$_6$H$_4$)$_3$ (0.0129 g, 0.04 mmol), (PhO)$_2$PO$_2$H (0.0011 g, 0.004 mmol), (±)-1a (0.0425 g, 1 mmol), water (72 µL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0218 g, 45%): oil substance; 80% ee (HPLC conditions: AS-H column, hexane/i-PrOH=98/2, 1.0 mL/min, λ=214 nm, t$_R$ (major)=6.5 min, t$_R$ (minor)=9.5 min).

Example 42

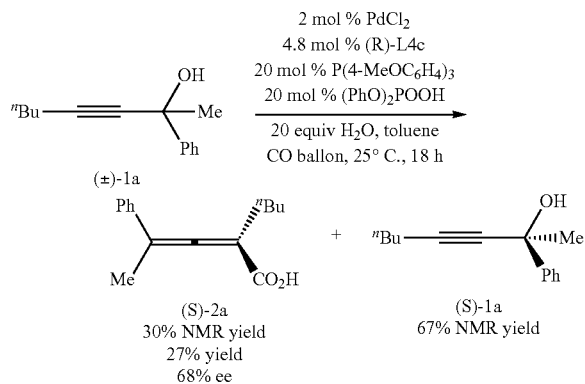

(S)-2a
30% NMR yield
27% yield
68% ee (S)-1a
67% NMR yield

Operations were conducted by referring to Example 1. PdCl$_2$ (0.0016 g, 0.004 mmol), (R)-L4c (0.0144 g, 0.012 mmol), P(4-MeOC$_6$H$_4$)$_3$ (0.0149 g, 0.04 mmol), (PhO)$_2$PO$_2$H (0.0011 g, 0.004 mmol), (±)-1a (0.0416 g, 1 mmol), water (72 µL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0128 g, 27%): oil substance; 68% ee (HPLC conditions: AS-H column, hexane/i-PrOH=98/2, 1.0 mL/min, λ=214 nm, t$_R$(major)=6.6 min, t$_R$(minor)=9.4 min).

Example 43

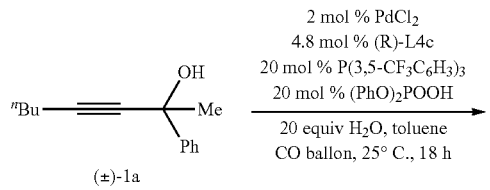

-continued

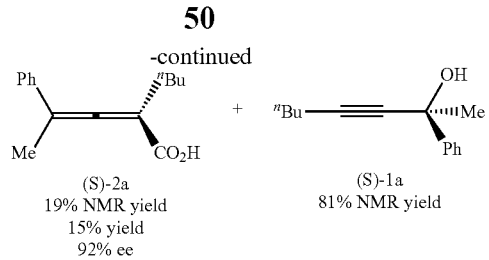

(S)-2a
19% NMR yield
15% yield
92% ee (S)-1a
81% NMR yield

Operations were conducted by referring to Example 1. PdCl$_2$ (0.0016 g, 0.004 mmol), (R)-L4c (0.0145 g, 0.012 mmol), P(3,5-CF$_3$C$_6$H$_3$)$_3$ (0.0271g, 0.04 mmol), (PhO)$_2$PO$_2$H (0.0012 g, 0.004 mmol), (±)-1a (0.0413 g, 1 mmol), water (72 µL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0071 g, 15%): oil substance; 92% ee (HPLC conditions: AS-H column, hexane/i-PrOH=98/2, 1.0 mL/min, λ=214 nm, t$_R$(major)=6.7 min, t$_R$(minor)=9.6 min).

Example 44

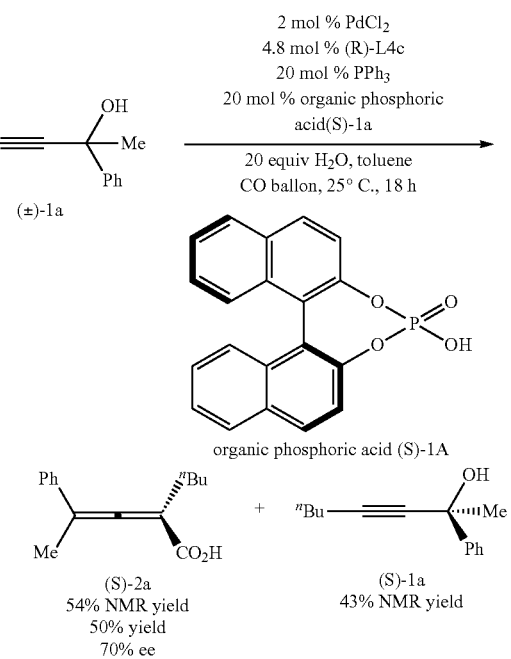

(S)-2a
54% NMR yield
50% yield
70% ee (S)-1a
43% NMR yield

Operations were conducted by referring to Example 1. PdCl$_2$ (0.0016 g, 0.004 mmol), (R)-L4c (0.0145 g, 0.012 mmol), PPh$_3$ (0.0105g, 0.04 mmol), organic phosphoric acid (S)-1A (0.0017 g, 0.004 mmol), (±)-1a (0.0397 g, 1 mmol), water (72 µL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0226g, 50%): oil substance; 70% ee (HPLC conditions: AS-H column, hexane/i-PrOH=98/2, 1.0 mL/min, λ=214 nm, t$_R$ (major)=6.6 min, t$_R$ (minor)=9.6 min).

Example 45

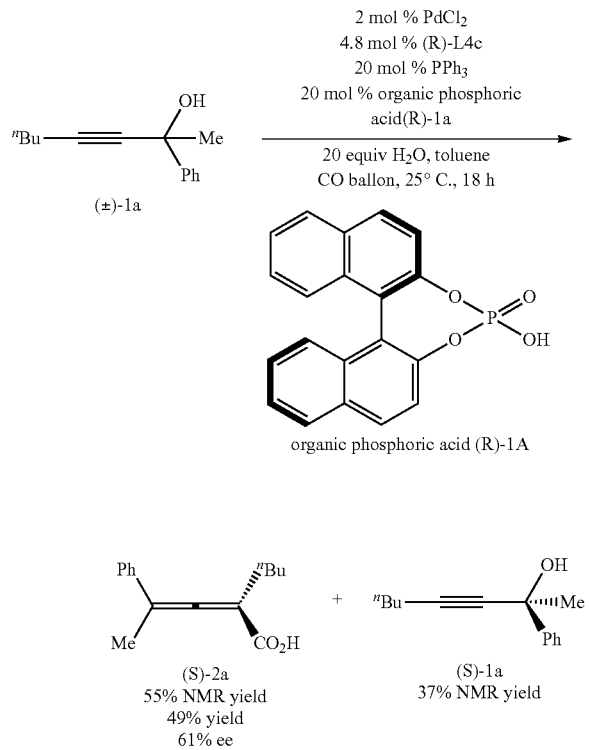

Operations were conducted by referring to Example 1. PdCl$_2$ (0.0015 g, 0.004 mmol), (R)-L4c (0.0143g, 0.012 mmol), PPh$_3$ (0.0106 g, 0.04 mmol), organic phosphoric acid (R)-1A (0.0014 g, 0.004 mmol), (±)-1a (0.041 g, 1 mmol), water (72 µL, d=1.0 g/mL, 0.072 g, 4 mmol), toluene (1 mL), reacted at 25° C. for 18 hours. Flash column chromatography (eluent: petroleum ether (60~90° C.)/ether/dichloromethane=30/1/1, petroleum ether (60~90° C.)/ethyl acetate=8/1) to afford a product: chiral allenic acid (S)-2a (0.0229g, 49%): oil substance; 61% ee (HPLC conditions: AS-H column, hexane/i-PrOH=98/2, 1.0 mL/min, λ=214 nm, $t_R$(major)=6.5 min, $t_R$(minor)=9.4 min).

Ordinary technicians in this field will understand that within the protection scope of the invention, it is feasible to modify, add and replace the above implementation cases, and none of them is beyond the protection scope of the invention.

What is claimed:

1. A method for preparing optically active axially chiral allenic acid compounds of formula 2 with greater than 90% enantiomeric excess, wherein, in the presence of palladium catalyst, chiral diphosphine ligand, monophosphine ligand and organic phosphoric acid, a tertiary propargyl alcohol with different substituents, carbon monoxide and water undergo asymmetric allylation reaction in an organic solvent through transition metal catalysis, preparing the optically active axially chiral allenic acid compounds in one-step synthesis, the reaction process has the following reaction equation (I):

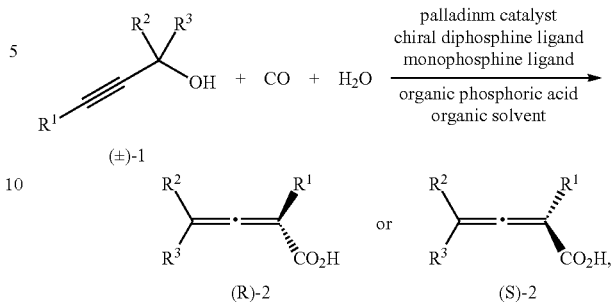

the different substituents of the tertiary propargyl alcohol with different substituents are $R^1$, $R^2$, $R^3$; wherein, $R^1$ is an alkyl, an alkyl with functional group, phenyl, aryl, heterocyclic group or naphthyl; $R^2$ is an alkyl, an alkyl with functional group, phenyl, aryl, heterocyclic group or naphthyl; $R^3$ is an alkyl, an alkyl with functional group, phenyl, aryl, heterocyclic group or naphthyl; the said aryl is a phenyl with electron-donating or electron-withdrawing substituents at the ortho, meta, and para positions; the said heterocyclic group is thienyl, furyl, or pyridyl with electron-donating or electron-withdrawing substituents.

2. The method of claim 1, wherein, $R^1$ is a C1-C20 alkyl, a C1-C20 alkyl with functional group at the end, phenyl, aryl, heterocyclic group or naphthyl; $R^2$ is a C1-C10 alkyl, a C1-C10 alkyl with functional group at the end, phenyl, aryl, heterocyclic group or naphthyl; $R^3$ is a C1-C10 alkyl, a C1-C10 alkyl with a functional group at the end, phenyl, aryl, heterocyclic group or naphthyl; wherein, the functional group of the C1-C20 alkyl or C1-C10 alkyl with a functional group at the end, is selected from the group consisting of carbon-carbon double bond, carbon-carbon triple bond, ester group, hydroxyl group, acyl group, acyloxy group, amide group, halogen, carboxyl group, or cyano group; the aryl is a phenyl with electron-withdrawing or electron-donating substituents at the ortho, meta, and para positions; the heterocyclic group is thienyl, furyl, naphthyl or pyridyl, with electron-withdrawing or electron-donating substituents; the electron-withdrawing substituent is halogen, nitro group, ester group, carboxyl group, acyl group, amide group, cyano group; the electron-donating substituent is alkyl, alkenyl, phenyl, alkoxy group, hydroxyl, or amino group.

3. The method of claim 1, wherein, the method comprises the following steps:
1) a palladium catalyst, a chiral diphosphine ligand, a monophosphine ligand and an organic phosphoric acid are added in sequence into a dried reaction tube, plugging the reaction tube with a rubber stopper, connecting a vacuum pump, degassing the reaction tube and refilling with argon three times, adding the tertiary propargyl alcohol, water, and a certain volume of organic solvent; freezing the reaction tube in liquid nitrogen bath, inserting carbon monoxide balloon into the dried reaction tube, degassing to remove the argon inside completely, and refilling with CO by the balloon of CO three times, returning the reaction system to room temperature, putting the reaction tube in the preset low-temperature bath or oil bath at −20-60° C.

and stirring for 4-36 hours; wherein the amount of the organic solvent is 1.0-10.0 mL to 1 mmol of tertiary propargyl alcohol;

2) after the completion of the reaction in step (1), raising the reaction tube from the low-temperature bath;

after returning to the room temperature, ethyl acetate is added into the reaction tube and a mixture obtained, filtering the mixture with silica gel short column, washing with a certain amount of ethyl acetate, concentrating, and subjecting to the flash column chromatography, so as to obtain the optically active axially chiral allenic acid compounds; wherein the amount of ethyl acetate is 1.0-100 mL to 1 mmol of tertiary propargyl alcohol (+1).

4. The method of claim 1, wherein the palladium catalysts are any one or more of dis-(allyl-palladium chloride), tetra-(triphenylphosphine) palladium, tri-(dibenzylidene-acetone) dipalladium, dis-(cinnamyl-palladium chloride), dis-(dibenzylidene-acetone) monopalladium, palladium chloride, palladium acetate, dis-(triphenylphosphine) palladium chloride and bis-(acetonitrile) palladium chloride.

5. The method of claim 1, wherein the chiral diphosphine ligand is selected from the group consisting of (R)-L2-(R)-L4 and its enantiomer (S)-L2-(S)-L4 in the following structures; wherein, "Ar" is a phenyl, an aryl, heterocyclic group or naphthyl; the aryl is a phenyl substituted by alkyl and/or alkoxy group at the ortho, meta, and para positions; the heterocyclic group is thienyl, furyl, naphthyl or pyridyl substituted by alkyl or alkoxy group, furan substituted by alkyl or alkoxy group, pyridine substituted by alkyl or alkoxy group;

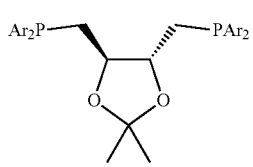

(R)-L2

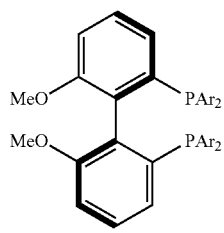

(R)-L3

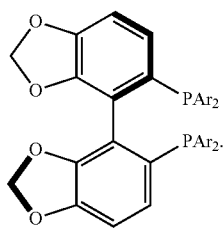

(R)-L4

6. The method of claim 5, wherein the chiral diphosphine ligand is selected from (R)-L4 and its enantiomer (S)-L4, the said structure of (R)-L4 is as follows:

wherein, "Ar" is 3,5-dialkyl-4-alkoxyphenyl, 3,5-dialkylphenyl or phenyl;

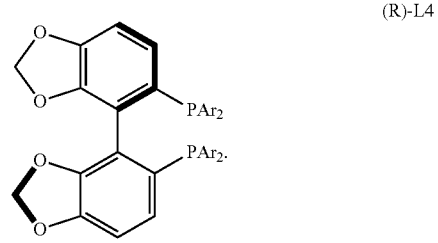

(R)-L4

7. The method of claim 1, wherein the monophosphine ligands are selected from the group consisting of tributylphosphine, tricyclohexylphosphine, triphenylphosphine, tris(ortho-methyl-phenyl)phosphine, tris(meta-methyl-phenyl) phosphine, tris(para-methyl-phenyl)phosphine, tris(para-methoxyphenyl)phosphine, tris(3,5-di-trifluoromethyl-phenyl) phosphine, and trifuryl-phosphine; and/or, the organic solvents are selected from the group consisting of N-methyl pyrrolidone, 1,4-dioxane, tetrahydrofuran, acetonitrile, methyl tert-butyl ether, chlorobenzene, toluene, trifluorotoluene, dichloromethane, 1,1-dichloroethane, 1,2-dichloroethane, chloroform, and acetic acid.

8. The method of claim 1, wherein the organic phosphoric acid is selected from any one or more of organic phosphoric acid 1, organic phosphoric acid 2, organic phosphoric acid 3, the structure of which is as follows; wherein, $R^1$ is hydrogen, C1-C6 alkyl, phenyl or aryl; the said aryl is a phenyl substituted by C1-C6 alkyl at the ortho, meta, and para positions; $R^2$ is C1-C6 alkyl, phenyl or aryl; the said aryl is a phenyl substituted by C1-C6 alkyl at the ortho, meta, and para positions,

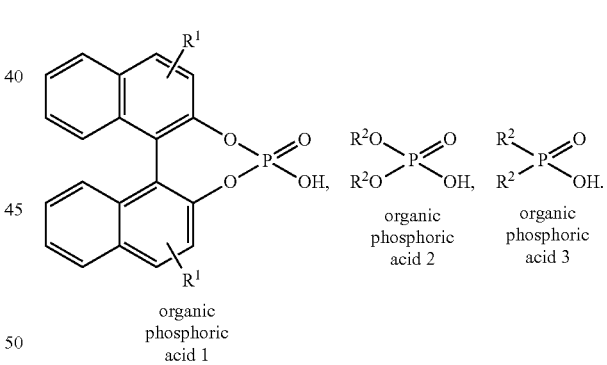

organic phosphoric acid 1, organic phosphoric acid 2, organic phosphoric acid 3.

9. The method of claim 1, wherein the molar ratio of tertiary propargyl alcohol (±1) with different substituents, water, palladium catalyst, chiral diphosphine ligand, monophosphine ligand and organic phosphoric acid in equation (I) of the present invention is 1.0: (1.0-30.0): (0.005-0.1): (0.005-0.1): (0.01-0.3): (0.01-0.3); and/or, the reaction temperature of the invention is 20-60° C.; and/or, the dosage of the organic solvent is 1.0-10.0 mL to 1 mmol of tertiary propargyl alcohol.

10. The method of claim 2, wherein the palladium catalysts are any one or more of dis-(allyl-palladium chloride), tetra-(triphenylphosphine) palladium, tri-(dibenzylidene-acetone) dipalladium, dis-(cinnamyl-palladium chloride), dis- (dibenzylidene-acetone) monopalladium, palladium chloride, palladium acetate, dis-(triphenylphosphine) palladium chloride and bis-(acetonitrile) palladium chloride.

11. The method of claim 3, wherein the palladium catalysts are any one or more of dis-(allyl-palladium chloride), tetra-(triphenylphosphine) palladium, tri-(dibenzylidene-acetone) dipalladium, dis-(cinnamyl-palladium chloride), dis-(dibenzylidene-acetone) monopalladium, palladium chloride, palladium acetate, dis-(triphenylphosphine) palladium chloride and bis-(acetonitrile) palladium chloride.

12. The method of claim 2, wherein the chiral diphosphine ligand is selected from one or more of (R)-L2-(R)-L4 or its enantiomer (S)-L2-(S)-L4 in the following structures; wherein, "Ar" is a phenyl, an aryl, heterocyclic group or naphthyl; the aryl is a phenyl substituted by alkyl and/or alkoxy group at the ortho, meta, and para positions; the heterocyclic group is thienyl, furyl, naphthyl or pyridyl substituted by alkyl or alkoxy group, furan substituted by alkyl or alkoxy group, pyridine substituted by alkyl or alkoxy group;

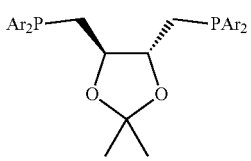

(R)-L2

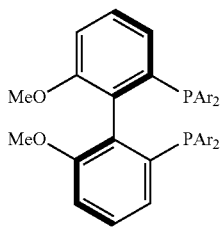

(R)-L3

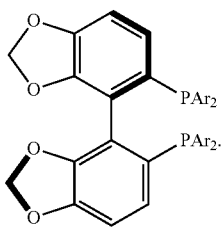

(R)-L4

13. The method of claim 3, wherein the chiral diphosphine ligand is selected from one or more of (R)-L2-(R)-L4 or its enantiomer (S)-L2-(S)-L4 in the following structures; wherein, "Ar" is a phenyl, an aryl, heterocyclic group or naphthyl; the aryl is a phenyl substituted by alkyl and/or alkoxy group at the ortho, meta, and para positions; the heterocyclic group is thienyl, furyl, naphthyl or pyridyl substituted by alkyl or alkoxy group, furan substituted by alkyl or alkoxy group, pyridine substituted by alkyl or alkoxy group;

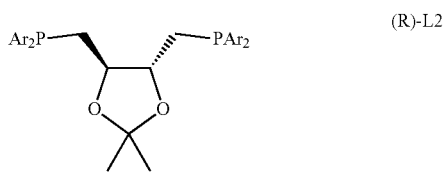

(R)-L2

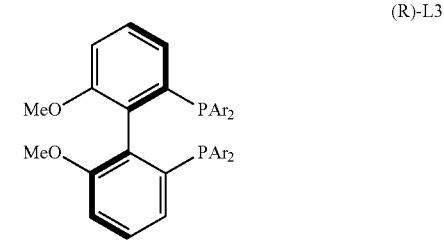

(R)-L3

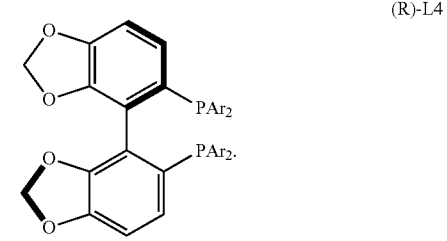

(R)-L4

14. The method of claim 2, wherein the monophosphine ligands are selected from the group consisting of tributylphosphine, tricyclohexylphosphine, triphenylphosphine, tris(ortho-methyl-phenyl)phosphine, tris(meta-methyl-phenyl) phosphine, tris(para-methyl-phenyl)phosphine, tris(para-methoxyphenyl)phosphine, tris(3,5-di-trifluoromethyl-phenyl) phosphine, trifuryl-phosphine; and, the organic solvents are selected from the group consisting of N-methyl pyrrolidone, 1,4-dioxane, tetrahydrofuran, acetonitrile, methyl tert-butyl ether, chlorobenzene, toluene, trifluorotoluene, dichloromethane, 1,1-dichloroethane, 1,2-dichloroethane, chloroform, and acetic acid.

15. The method of claim 3, wherein the monophosphine ligands are selected from the group consisting of tributylphosphine, tricyclohexylphosphine, triphenylphosphine, tris(ortho-methyl-phenyl)phosphine, tris(meta-methyl-phenyl) phosphine, tris(para-methyl-phenyl)phosphine, tris(para-methoxyphenyl)phosphine, tris(3,5-di-trifluoromethyl-phenyl) phosphine, and trifuryl-phosphine; and/or, the organic solvents are selected from the group consisting of N-methyl pyrrolidone, 1,4-dioxane, tetrahydrofuran, acetonitrile, methyl tert-butyl ether, chlorobenzene, toluene, trifluorotoluene, dichloromethane, 1,1-dichloroethane, 1,2-dichloroethane, chloroform, and acetic acid.

16. The method of claim 2, wherein the organic phosphoric acid is selected from any one or more of organic phosphoric acid 1, organic phosphoric acid 2, organic phosphoric acid 3, the structure of which is as follows; wherein, $R^1$ is hydrogen, C1-C6 alkyl, phenyl or aryl; the said aryl is a phenyl substituted by C1-C6 alkyl at the ortho, meta, and para positions; $R^2$ is C1-C6 alkyl, phenyl or aryl; the said aryl is a phenyl substituted by C1-C6 alkyl at the ortho, meta, and para positions,

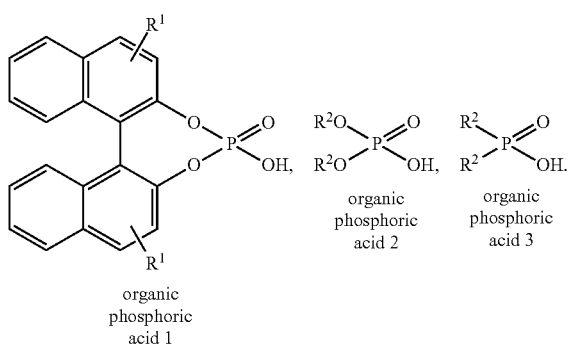

organic phosphoric acid 1, organic phosphoric acid 2, organic phosphoric acid 3.

17. The method of claim 3, wherein the organic phosphoric acid is selected from any one or more of organic phosphoric acid 1, organic phosphoric acid 2, organic phosphoric acid 3, the structure of which is as follows; wherein, $R^1$ is hydrogen, C1-C6 alkyl, phenyl or aryl; the said aryl is a phenyl substituted by C1-C6 alkyl at the ortho, meta, and para positions; $R^2$ is C1-C6 alkyl, phenyl or aryl; the said aryl is a phenyl substituted by C1-C6 alkyl at the ortho, meta, and para positions,

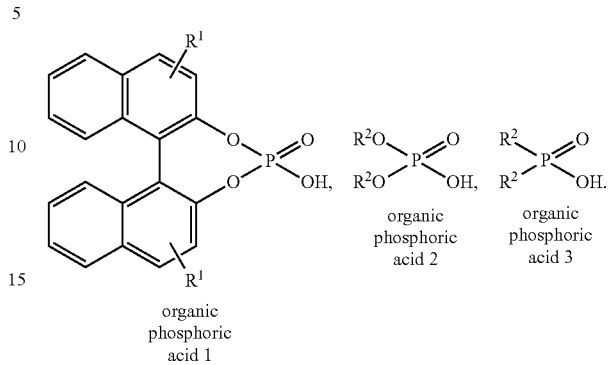

organic phosphoric acid 1, organic phosphoric acid 2, organic phosphoric acid 3.

* * * * *